(12) United States Patent
Haga et al.

(10) Patent No.: US 12,661,036 B2
(45) Date of Patent: Jun. 23, 2026

(54) DETECTION DEVICE

(71) Applicant: Magnolia White Corporation, Tokyo (JP)

(72) Inventors: Yuta Haga, Tokyo (JP); Ayato Kitamura, Tokyo (JP)

(73) Assignee: Magnolia White Corporation, Tokyo (JP)

( * ) Notice: Subject to any disclaimer, the term of this patent is extended or adjusted under 35 U.S.C. 154(b) by 800 days.

(21) Appl. No.: 18/066,423

(22) Filed: Dec. 15, 2022

(65) Prior Publication Data

US 2023/0200690 A1 Jun. 29, 2023

(30) Foreign Application Priority Data

Dec. 23, 2021 (JP) ................................. 2021-209992

(51) Int. Cl.
*A61B 5/1455* (2006.01)
(52) U.S. Cl.
CPC ................................. *A61B 5/1455* (2013.01)
(58) Field of Classification Search
CPC . A61B 5/0059; A61B 5/0205; A61B 5/02433; A61B 5/1455; A61B 5/14551; A61B 5/14552; A61B 5/15447; A61B 5/14532; A61B 5/7214; A61B 5/7221; A61B 2562/0238; A61B 2562/04; A61B 2562/164
See application file for complete search history.

(56) References Cited

U.S. PATENT DOCUMENTS

| | | | |
|---|---|---|---|
| 2003/0009091 A1* | 1/2003 | Edgar, Jr. ........... | A61B 5/14551 600/323 |
| 2012/0253153 A1* | 10/2012 | Trumble ............ | A61B 5/14551 600/324 |
| 2013/0261415 A1* | 10/2013 | Ashe .................. | A61B 5/14552 600/323 |
| 2017/0347902 A1* | 12/2017 | Van Gool .......... | A61B 5/02427 |
| 2018/0132766 A1* | 5/2018 | Lee ....................... | A61B 5/1455 |
| 2023/0015361 A1 | 1/2023 | Kato et al. | |

FOREIGN PATENT DOCUMENTS

| | | |
|---|---|---|
| JP | 2014-198202 A | 10/2014 |
| JP | 2019-180861 A | 10/2019 |
| JP | 2021-157657 A | 10/2021 |

OTHER PUBLICATIONS

Office Action issued in related Japanese Patent Application No. 2021-209992, mailed on Mar. 25, 2025 and English translation of same. 6 pages.

* cited by examiner

*Primary Examiner* — Chu Chuan Liu
(74) *Attorney, Agent, or Firm* — K&L Gates LLP

(57) ABSTRACT
According to an aspect, a detection device includes: a sensor having a detection area divided into a plurality of partial detection areas; and a detector configured to extract, from among the partial detection areas, one or more partial detection areas in each of which a signal strength of data satisfying a predetermined condition is acquired, and acquire biometric data on an object to be detected based on detection signals detected in a biometric data acquisition area including the extracted one or more partial detection areas.

14 Claims, 30 Drawing Sheets

DATA VALUE

TIME

FIG.19

| Raw(1)<1, 1> | Raw(1)<2, 1> | $\cdots$ | Raw(1)<M, 1> |
|---|---|---|---|
| Raw(1)<1, 2> | Raw(1)<2, 2> | $\cdots$ | Raw(1)<M, 2> |
| : | : | Raw(1)<m, n> | : |
| Raw(1)<1, N> | Raw(1)<2, N> | $\cdots$ | Raw(1)<M, N> |

| Raw(2)<1, 1> | Raw(2)<2, 1> | $\cdots$ | Raw(2)<M, 1> |
|---|---|---|---|
| Raw(2)<1, 2> | Raw(2)<2, 2> | $\cdots$ | Raw(2)<M, 2> |
| : | : | Raw(2)<m, n> | : |
| Raw(2)<1, N> | Raw(2)<2, N> | $\cdots$ | Raw(2)<M, N> |

:

| Raw(F)<1, 1> | Raw(F)<2, 1> | $\cdots$ | Raw(F)<M, 1> |
|---|---|---|---|
| Raw(F)<1, 2> | Raw(F)<2, 2> | $\cdots$ | Raw(F)<M, 2> |
| : | : | Raw(F)<m, n> | : |
| Raw(F)<1, N> | Raw(F)<2, N> | $\cdots$ | Raw(F)<M, N> |

BAA          PAA          AA

| Raw<m-2, n-2> | Raw<m-1, n-2> | Raw<m, n-2> | Raw<m+1, n-2> | Raw<m+2, n-2> |
| Raw<m-2, n-1> | Raw<m-1, n-1> | Raw<m, n-1> | Raw<m+1, n-1> | Raw<m+2, n-1> |
| Raw<m-2, n> | Raw<m-1, n> | Raw<m, n> | Raw<m+1, n> | Raw<m+2, n> |
| Raw<m-2, n+1> | Raw<m-1, n+1> | Raw<m, n+1> | Raw<m+1, n+1> | Raw<m+2, n+1> |
| Raw<m-2, n+2> | Raw<m-1, n+2> | Raw<m, n+2> | Raw<m+1, n+2> | Raw<m+2, n+2> |

Smax(m, n)

BAA        PAA

| Raw<m-3, n-3> | Raw<m-2, n-3> | Raw<m-1, n-3> | Raw<m, n-3> | Raw<m+1, n-3> | Raw<m+2, n-3> | Raw<m+3, n-3> |
| Raw<m-3, n-2> | Raw<m-2, n-2> | Raw<m-1, n-2> | Raw<m, n-2> | Raw<m+1, n-2> | Raw<m+2, n-2> | Raw<m+3, n-2> |
| Raw<m-3, n-1> | Raw<m-2, n-1> | Raw<m-1, n-1> | Raw<m, n-1> | Raw<m+1, n-1> | Raw<m+2, n-1> | Raw<m+3, n-1> |
| Raw<m-3, n> | Raw<m-2, n> | Raw<m-1, n> | Raw<m, n> | Raw<m+1, n> | Raw<m+2, n> | Raw<m+3, n> |
| Raw<m-3, n+1> | Raw<m-2, n+1> | Raw<m-1, n+1> | Raw<m, n+1> | Raw<m+1, n+1> | Raw<m+2 ,n+1> | Raw<m+3, n+1> |
| Raw<m-3, n+2> | Raw<m-2, n+2> | Raw<m-1, n+2> | Raw<m, n+2> | Raw<m+1, n+2> | Raw<m+2, n+2> | Raw<m+3, n+2> |
| Raw<m-3, n+3> | Raw<m-2, n+3> | Raw<m-1, n+3> | Raw<m, n+3> | Raw<m+1, n+3> | Raw<m+2, n+3> | Raw<m+3, n+3> |

Smax(m, n)

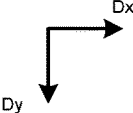

| Dp_add<1, 1> | Dp_add<2, 1> | ⋯ | Dp_add<M, 1> |
|---|---|---|---|
| Dp_add<1, 2> | Dp_add<2, 2> | ⋯ | Dp_add<M, 2> |
| : | : | Dp_add<m, n> | : |
| Dp_add<1, N> | Dp_add<2, N> | ⋯ | Dp_add<M, N> |

FIG.28B

| Dp_cnt<1, 1> | Dp_cnt<2, 1> | ⋯ | Dp_cnt<M, 1> |
|---|---|---|---|
| Dp_cnt<1, 2> | Dp_cnt<2, 2> | ⋯ | Dp_cnt<M, 2> |
| : | : | Dp_cnt<m, n> | : |
| Dp_cnt<1, N> | Dp_cnt<2, N> | ⋯ | Dp_cnt<M, N> |

DETECTION DEVICE

CROSS-REFERENCE TO RELATED APPLICATION

This application claims the benefit of priority from Japanese Patent Application No. 2021-209992 filed on Dec. 23, 2021, the entire contents of which are incorporated herein by reference.

BACKGROUND

1. Technical Field

What is disclosed herein relates to a detection device.

2. Description of the Related Art

Detection devices are known that emit light into a body through the skin and acquire an oxygen saturation level in blood (hereinafter, called "blood oxygen saturation level" ($SpO_2$)) based on transcutaneous data acquired by detecting light transmitted through or reflected by arteries. The blood oxygen saturation level ($SpO_2$) refers to a ratio of an amount of oxygen actually bound to hemoglobin to the total amount of oxygen under the assumption that the oxygen is bound to all the hemoglobin in the blood. When acquiring the blood oxygen saturation level ($SpO_2$), for example, a pulse wave acquired by infrared light and a pulse wave acquired by red light are used (refer to Japanese Patent Application Laid-open Publication No. 2019-180861, for example).

The transcutaneous data might not be acquired at high accuracy depending on the distribution of subcutaneous blood vessels. In addition, the transcutaneous data includes noise components caused by disturbances and body movements of a subject.

For the foregoing reasons, there is a need for a detection device capable of acquiring accurate data on a living body.

SUMMARY

According to an aspect, a detection device includes: a sensor having a detection area divided into a plurality of partial detection areas; and a detector configured to extract, from among the partial detection areas, one or more partial detection areas in each of which a signal strength of data satisfying a predetermined condition is acquired, and acquire biometric data on an object to be detected based on detection signals detected in a biometric data acquisition area including the extracted one or more partial detection areas.

BRIEF DESCRIPTION OF THE DRAWINGS

FIG. 10 is an explanatory diagram for explaining a relation between driving of the sensor of the detection device and lighting operations of light sources;

FIG. 14 is a timing waveform diagram illustrating the operation example of the detection device according to the embodiment;

FIG. 19 is a chart illustrating detection values for F frames in the respective partial detection areas in the detection area that are temporarily stored in a storage;

FIG. 23C is a diagram illustrating still another specific example of the biometric data acquisition area;

FIG. 28A is a chart illustrating accumulated peak values temporarily stored in the storage; and FIG. 28B is a chart illustrating peak accumulation counts temporarily stored in the storage.

DETAILED DESCRIPTION

Figure 1:
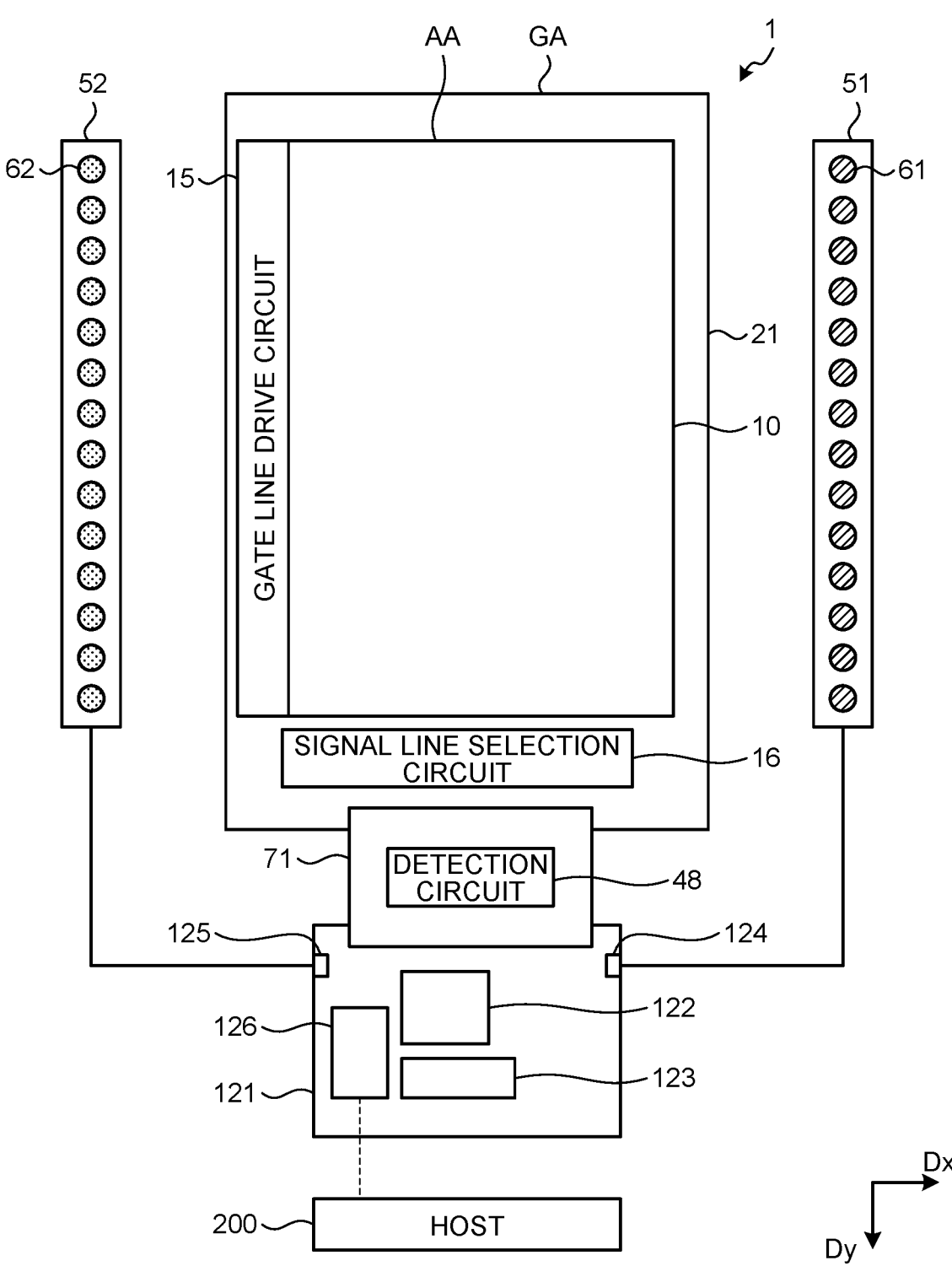
FIG. 1 is a plan view illustrating a detection device according to an embodiment.

The following describes modes (embodiments) for carrying out the present invention in detail with reference to the drawings. The present invention is not limited to the description of the embodiments given below. Components described below include those easily conceivable by those skilled in the art or those substantially identical thereto. In addition, the components described below can be combined as appropriate. What is disclosed herein is merely an example, and the present invention naturally encompasses appropriate modifications easily conceivable by those skilled in the art while maintaining the gist of the invention. To further clarify the description, the drawings may schematically illustrate, for example, widths, thicknesses, and shapes of various parts as compared with actual aspects thereof. However, they are merely examples, and interpretation of the present invention is not limited thereto. The same component as that described with reference to an already mentioned drawing is denoted by the same reference numeral through the description and the drawings, and detailed description thereof may not be repeated where appropriate.

In this disclosure, when an element is described as being "on" another element, the element can be directly on the other element, or there can be one or more elements between the element and the other element.

FIG. 1 is a plan view illustrating a detection device according to an embodiment. As illustrated in FIG. 1, a detection device 1 includes a sensor base member 21, a sensor 10, a gate line drive circuit 15, a signal line selection circuit 16, a detection circuit 48, a control circuit 122, a power supply circuit 123, first light sources 61, and second light sources 62. FIG. 1 illustrates an example in which a first light source base member 51 is provided with the first light sources 61 and a second light source base member 52 is provided with the second light sources 62. However, the arrangement of the first and the second light sources 61 and 62 illustrated in FIG. 1 is merely an example and can be changed as appropriate. For example, the first and the second light sources 61 and 62 may be arranged on each of the first and the second light source base members 51 and 52. In this case, a group including the first light sources 61 and a group including the second light sources 62 may be arranged in a second direction Dy, or the first and the second light sources 61 and 62 may be alternately arranged in the second direction Dy. The first and the second light sources 61 and 62 may be provided on one light source base member, or three or more light source base members. A specific example of the arrangement of the first and the second light sources 61 and 62 will be described later.

The detection device 1 is electrically coupled to a host 200. The host 200 is, for example, a higher-level control device for an apparatus (not illustrated) to which the detection device 1 is applied. The host 200 performs a predetermined biometric information acquisition process based on data output from the detection device 1.

The sensor base member 21 is electrically coupled to a control substrate 121 through a flexible printed circuit board 71. The flexible printed circuit board 71 is provided with the detection circuit 48. The control substrate 121 is provided with the control circuit 122, the power supply circuit 123, and an output circuit 126.

The control circuit 122 includes, for example, a control integrated circuit (IC) that outputs logic control signals. The control circuit 122 may be, for example, a programmable logic device (PLD) such as a field-programmable gate array (FPGA).

The control circuit 122 supplies control signals to the sensor 10, the gate line drive circuit 15, and the signal line selection circuit 16 to control a detection operation of the sensor 10. The control circuit 122 supplies control signals to the first and the second light sources 61 and 62 to control lighting and non-lighting of the first and the second light sources 61 and 62.

The power supply circuit 123 supplies voltage signals including, for example, a sensor power supply potential VDDSNS (refer to FIG. 4) to the sensor 10, the gate line drive circuit 15, and the signal line selection circuit 16. The power supply circuit 123 supplies a power supply voltage to the first and the second light sources 61 and 62.

The output circuit 126 is, for example, a Universal Serial Bus (USB) controller IC and controls communication between the control circuit 122 and the host 200.

The sensor base member 21 has a detection area AA and a peripheral area GA. The detection area AA is an area provided with a plurality of optical sensors PD (refer to FIG. 4) included in the sensor 10. The peripheral area GA is an area between the outer perimeter of the detection area AA and the ends of the sensor base member 21 and is an area not provided with the optical sensors PD.

The gate line drive circuit 15 and the signal line selection circuit 16 are provided in the peripheral area GA. Specifically, the gate line drive circuit 15 is provided in an area extending along the second direction Dy in the peripheral area GA. The signal line selection circuit 16 is provided in an area extending along a first direction Dx in the peripheral area GA and is provided between the sensor 10 and the detection circuit 48.

The first direction Dx is one direction in a plane parallel to the sensor base member 21. The second direction Dy is one direction in the plane parallel to the sensor base member 21 and is a direction orthogonal to the first direction Dx. The second direction Dy may non-orthogonally intersect the first direction Dx. A third direction Dz is a direction orthogonal to the first direction Dx and the second direction Dy and is a direction normal to the sensor base member 21.

The first light sources 61 are provided on the first light source base member 51 and are arranged along the second direction Dy. The second light sources 62 are provided on the second light source base member 52 and are arranged along the second direction Dy. The first light source base member 51 and the second light source base member 52 are electrically coupled, through terminals 124 and 125 provided on the control substrate 121, to the control circuit 122 and the power supply circuit 123.

For example, inorganic light-emitting diodes (LEDs) or organic electroluminescent (EL) diodes (organic light-emitting diodes (OLEDs)) are used as the first and the second light sources 61 and 62. The first and the second light sources 61 and 62 emit first light and second light, respectively, having different wavelengths.

The first light emitted from the first light sources 61 is reflected, for example, on a surface of an object to be detected, such as a finger or a wrist of a subject, and is incident on the sensor 10. As a result, the sensor 10 can detect a fingerprint by detecting a shape of asperities on the surface of a finger Fg or the like. The second light emitted from the second light sources 62 is, for example, reflected in the finger Fg or the like, or transmitted through the finger Fg or the like, and is incident on the sensor 10. As a result, the sensor 10 can detect information on a living body in the finger, the wrist, and the like of the subject. Examples of the information on the living body include pulse waves, pulsation, and a vascular image of the subject. That is, the detection device 1 may be configured as a fingerprint detection device to detect a fingerprint or a vein detection device to detect a vascular pattern of, for example, veins.

The first light may have a wavelength of from 520 nm to 600 nm, for example, a wavelength of approximately 550 nm, and the second light may have a wavelength of from 780 nm to 950 nm, for example, a wavelength of approximately 850 nm. In this case, the first light is visible light in blue or green (blue light or green light), and the second light is infrared light. The sensor 10 can detect a fingerprint based on the first light emitted from the first light sources 61. The second light emitted from the second light sources 62 is reflected in, or transmitted through or absorbed by the object to be detected, and is incident on the sensor 10. As a result, the sensor 10 can detect the biometric data such as the pulse waves and the vascular image (vascular pattern) as the information on the living body in the finger, the wrist, and the like of the subject.

Alternatively, the first light may have a wavelength of from 600 nm to 700 nm, for example, approximately 660 nm, and the second light may have a wavelength of from 780 nm to 950 nm, for example, approximately 850 nm. In this case, the sensor 10 can detect a blood oxygen level in addition to the pulse waves, the pulsation, and the vascular image as the information on the living body based on the first light emitted from the first light sources 61 and the second light emitted from the second light sources 62. As described above, the detection device 1 includes the first and the second light sources 61 and 62, and performs the detection based on the first light and the detection based on the second light, and thereby can detect the various types of information on the living body.

Figure 2:
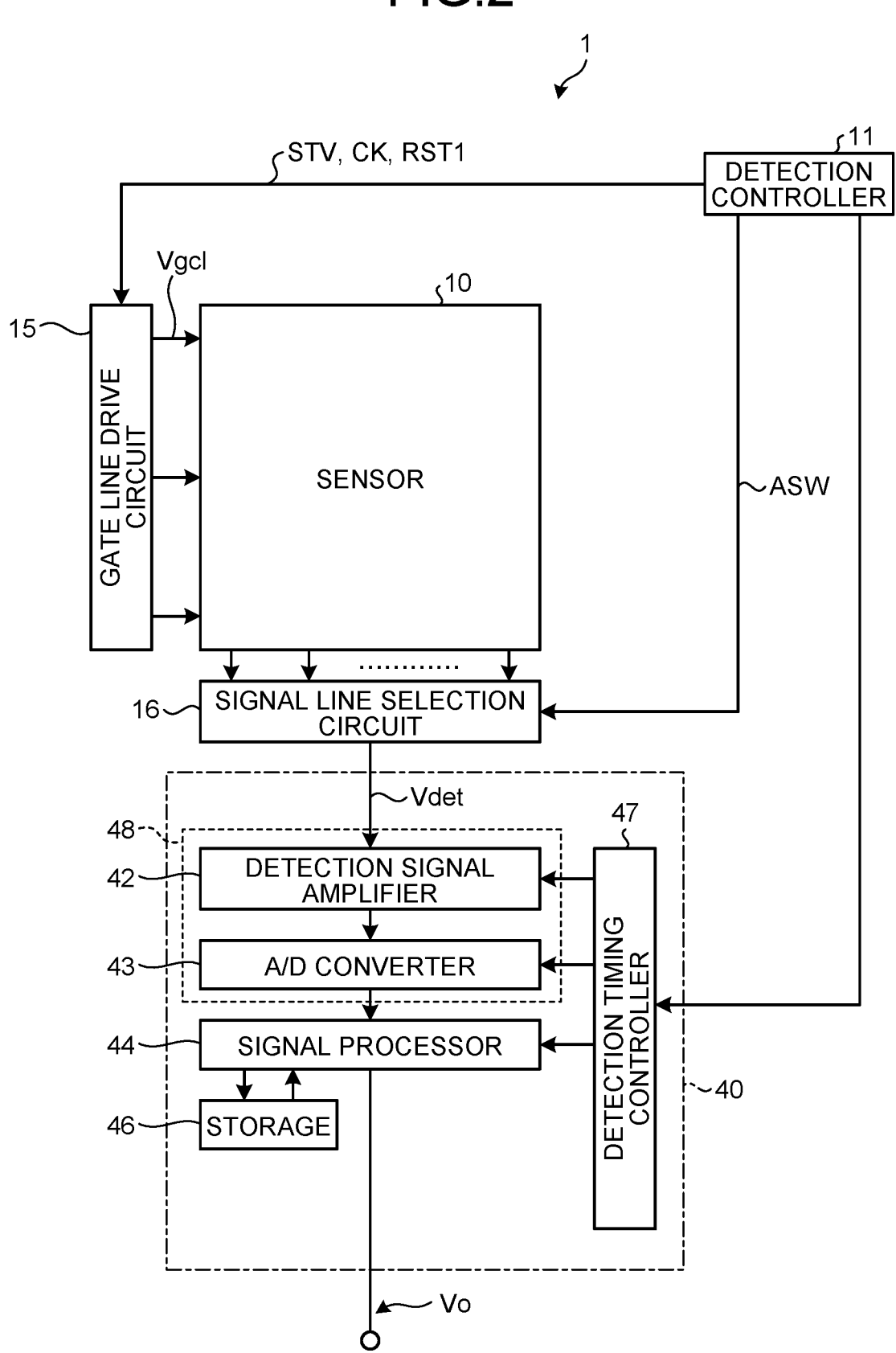
FIG. 2 is a block diagram illustrating a configuration example of the detection device according to the embodiment.

FIG. 2 is a block diagram illustrating a configuration example of the detection device according to the embodiment. As illustrated in FIG. 2, the detection device 1 further includes a detection controller (detection control circuit) 11 and a detector (detection signal processing circuit) 40.

The sensor 10 includes the optical sensors PD. Each of the optical sensors PD included in the sensor 10 is an organic photodiode (OPD) and outputs an electrical signal corresponding to light emitted thereto as a detection signal Vdet to the signal line selection circuit 16. The sensor 10 performs the detection in response to a gate drive signal Vgcl supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals including, for example, a start signal STV, a clock signal CK, and a reset signal RST1 to the gate line drive circuit 15. The detection controller 11 also supplies various control signals including, for example, a selection signal ASW to the signal line selection circuit 16. The detection controller 11 supplies various control signals to the first and the second light sources 61 and 62 to control the lighting and the non-lighting of each group of the first and the second light sources 61 and 62.

The gate line drive circuit 15 is a circuit that drives a plurality of gate lines GCL (refer to FIG. 3) based on the various control signals. The gate line drive circuit 15 sequentially or simultaneously selects the gate lines GCL and supplies the gate drive signals Vgcl to the selected gate lines GCL. Through this operation, the gate line drive circuit 15 selects the optical sensors PD coupled to the gate lines GCL.

Figure 3:
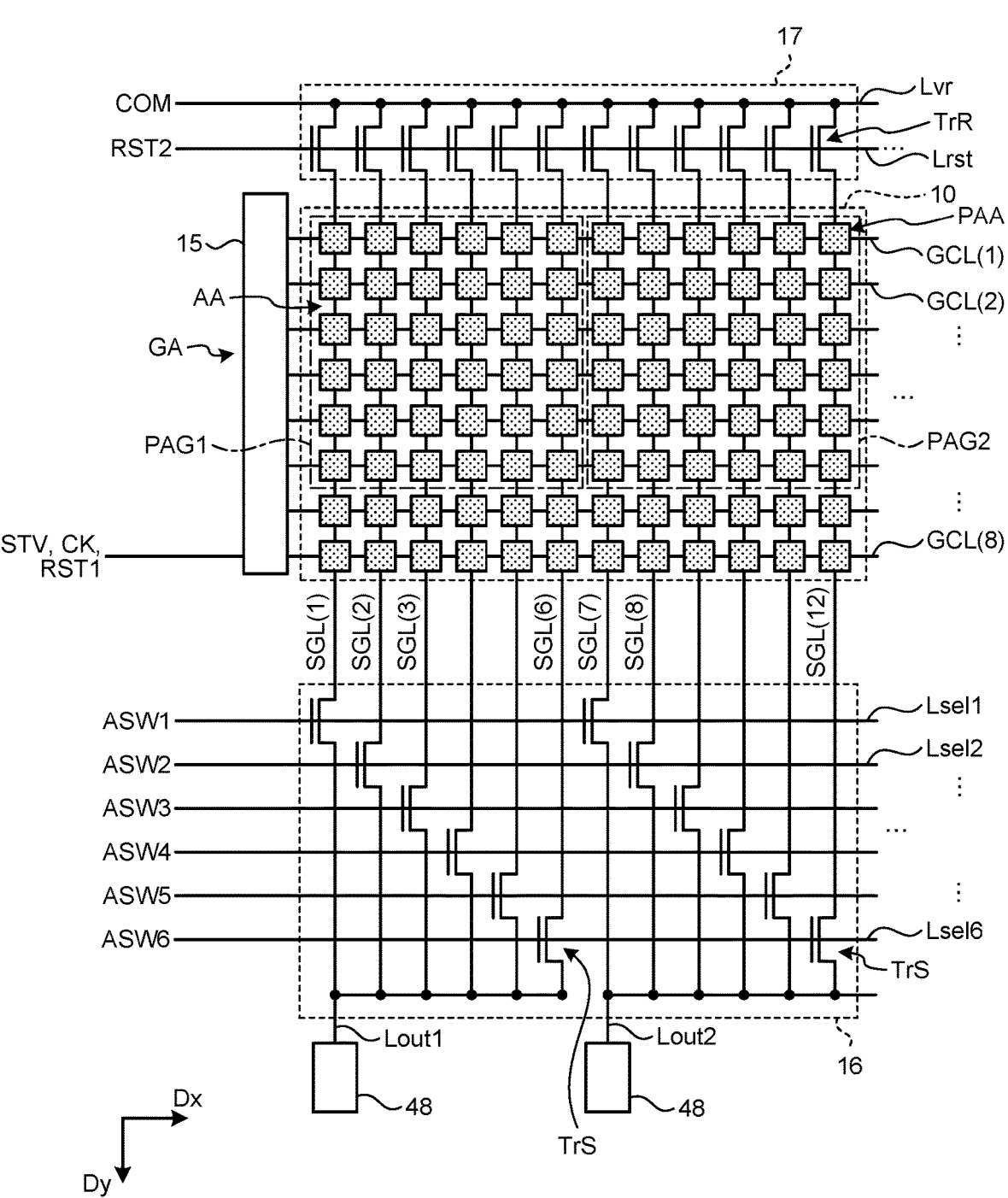
FIG. 3 is a circuit diagram illustrating the detection device.

The signal line selection circuit 16 is a switch circuit that sequentially or simultaneously selects a plurality of signal lines SGL (refer to FIG. 3). The signal line selection circuit 16 is, for example, a multiplexer. The signal line selection circuit 16 electrically couples the selected signal lines SGL to the detection circuit 48 based on the selection signal ASW supplied from the detection controller 11. By this operation, the signal line selection circuit 16 outputs the detection signals Vdet of the optical sensors PD to the detector 40.

The detector 40 includes the detection circuit 48, a signal processor (signal processing circuit) 44, a storage (storage circuit) 46, and a detection timing controller (detection timing control circuit) 47. Based on a control signal supplied from the detection controller 11, the detection timing controller 47 controls the detection circuit 48 and the signal processor 44 so as to operate in synchronization with each other.

The detection circuit 48 generates a detection value of each of the optical sensors PD based on the detection signal of the optical sensor PD output from the sensor 10. The detection circuit 48 is, for example, an analog front-end (AFE) circuit.

The detection circuit 48 is a signal processing circuit having functions of at least a detection signal amplifier 42 and an analog-to-digital (A/D) converter 43. The detection signal amplifier 42 amplifies the detection signals Vdet. The A/D converter 43 converts analog signals output from the detection signal amplifier 42 into digital signals.

In the present disclosure, the control circuit 122 includes the signal processor 44 and the storage 46.

The signal processor 44 acquires the biometric data for generating the information on the living body based on the detection values of the optical sensors PD output from the detection circuit 48. In the present disclosure, the information on the living body includes the pulse waves acquired using the infrared light and/or the red light, for example.

The storage 46 temporarily stores therein signals processed by the signal processor 44. In the present disclosure, the storage 46 also stores therein information on a biometric data acquisition area that is set in a biometric data acquisition area setting process (to be described later) when the signal processor 44 acquires the biometric data and stores therein various types of setting information. In an aspect of the present disclosure, the storage 46 may include, for example, a random-access memory (RAM), a read-only memory (ROM), and an electrically erasable programmable read-only memory (EEPROM). The storage 46 may be a register circuit, for example.

The following describes a circuit configuration example of the detection device 1. FIG. 3 is a circuit diagram illustrating the detection device. As illustrated in FIG. 3, the sensor 10 has a plurality of partial detection areas PAA arranged in a matrix having a row-column configuration. Each of the partial detection areas PAA is provided with the optical sensor PD.

The gate lines GCL extend in the first direction Dx and are each coupled to the partial detection areas PAA arranged in the first direction Dx. A plurality of gate lines GCL(1), GCL(2), . . . , GCL(8) are arranged in the second direction Dy and are each coupled to the gate line drive circuit 15. In the following description, the gate lines GCL(1), GCL(2), . . . , GCL(8) will each be simply referred to as the gate line GCL when they need not be distinguished from one another. For ease of understanding of the description, FIG. 3 illustrates eight gate lines GCL. However, this is merely an example, and M gate lines GCL (where M is a natural number, for example, M=256) may be arranged.

The signal lines SGL extend in the second direction Dy and are each coupled to the optical sensor PD of the partial detection areas PAA arranged in the second direction Dy. A plurality of signal lines SGL(1), SGL(2), . . . , SGL(12) are arranged in the first direction Dx and are each coupled to the signal line selection circuit 16 and a reset circuit 17. In the following description, the signal lines SGL(1), SGL(2), . . . , SGL(12) will each be simply referred to as the signal line SGL when they need not be distinguished from one another.

For ease of understanding of the description, 12 signal lines SGL are illustrated. However, this is merely an example, and N signal lines SGL (where N is a natural number, for example, N=252) may be arranged. In FIG. 3, the sensor 10 is provided between the signal line selection circuit 16 and the reset circuit 17. The present disclosure is not limited thereto. The signal line selection circuit 16 and the reset circuit 17 may be coupled to ends of the signal lines SGL in the same direction.

The gate line drive circuit 15 receives the various control signals such as the start signal STV, the clock signal CK, and the reset signal RST1 from the control circuit 122 (refer to FIG. 1). The gate line drive circuit 15 sequentially selects the gate lines GCL(1), GCL(2), . . . , GCL(8) in a time-division manner based on the various control signals. The gate line drive circuit 15 supplies the gate drive signal Vgcl to the selected one of the gate lines GCL. This operation supplies the gate drive signal Vgcl to a plurality of first switching elements Tr coupled to the gate line GCL, and corresponding ones of the partial detection areas PAA arranged in the first direction Dx are selected as detection targets.

The gate line drive circuit 15 may perform different driving for each of detection modes including the detection of a fingerprint and the detection of a plurality of different items of information on the living body (including, for example, the pulse waves, the pulsation, the vascular image, and the blood oxygen level, which are hereinafter called also simply "biometric information"). For example, the gate line drive circuit 15 may drive more than one of the gate lines GCL collectively.

Specifically, the gate line drive circuit 15 simultaneously selects a predetermined number of the gate lines GCL from among the gate lines GCL(1), GCL(2), . . . , GCL(8) based on the control signals. For example, the gate line drive circuit 15 simultaneously selects six of the gate lines GCL (1) to GCL(6) and supplies thereto the gate drive signals Vgcl. The gate line drive circuit 15 supplies the gate drive signals Vgcl through the selected six gate lines GCL to the first switching elements Tr. By this operation, block units PAG1 and PAG2 each including corresponding ones of the partial detection areas PAA arranged in the first direction Dx and the second direction Dy, are selected as the respective detection targets. The gate line drive circuit 15 drives the predetermined number of the gate lines GCL collectively and sequentially supplies the gate drive signals Vgcl in units of the predetermined number of the gate lines GCL.

The signal line selection circuit 16 includes a plurality of selection signal lines Lsel, a plurality of output signal lines Lout, and third switching elements TrS. The third switching elements TrS are provided corresponding to the signal lines SGL. Six signal lines SGL(1), SGL(2), . . . , SGL(6) are coupled to a common output signal line Lout1. Six signal lines SGL(7), SGL(8), . . . , SGL(12) are coupled to a common output signal line Lout2. The output signal lines Lout1 and Lout2 are each coupled to the detection circuit 48.

The signal lines SGL(1), SGL(2), . . . , SGL(6) are grouped into a first signal line block, and the signal lines SGL(7), SGL(8), . . . , SGL(12) are grouped into a second signal line block. The selection signal lines Lsel are coupled to the gates of the respective third switching elements TrS included in one of the signal line blocks. One of the selection signal lines Lsel is coupled to the gates of the third switching elements TrS in the signal line blocks.

Specifically, selection signal lines Lsel1, Lsel2, . . . , Lsel6 are coupled to the third switching elements TrS corresponding to the signal lines SGL(1), SGL(2), . . . , SGL(6), respectively. The selection signal line Lsel1 is coupled to the third switching element TrS corresponding to the signal line SGL(1) and the third switching element TrS corresponding to the signal line SGL(7). The selection signal line Lsel2 is coupled to the third switching element TrS corresponding to the signal line SGL(2) and the third switching element TrS corresponding to the signal line SGL(8).

The control circuit 122 (refer to FIG. 1) sequentially supplies the selection signal ASW to the selection signal lines Lsel. This operation causes the signal line selection circuit 16 to operate the third switching elements TrS to sequentially select the signal lines SGL in one of the signal line blocks in a time-division manner. The signal line selection circuit 16 selects one of the signal lines SGL in each of the signal line blocks. With the above-described configuration, the detection device 1 can reduce the number of integrated circuits (ICs) including the detection circuit 48 or the number of terminals of the ICs.

The signal line selection circuit 16 may couple more than one of the signal lines SGL collectively to the detection circuit 48. Specifically, the control circuit 122 (refer to FIG. 1) simultaneously supplies the selection signal ASW to the selection signal lines Lsel. The signal line selection circuit 16 operates the third switching elements TrS to select the signal lines SGL (for example, six of the signal lines SGL) in one of the signal line blocks and couples the signal lines SGL to the detection circuit 48. As a result, signals detected in each of the block units PAG1 and PAG2 are output to the detection circuit 48. In this case, the signals from the partial detection areas PAA (optical sensors PD) included in each of the block units PAG1 and PAG2 are integrated and output to the detection circuit 48.

The detection is performed for each of the block units PAG1 and PAG2 by the operations of the gate line drive circuit 15 and the signal line selection circuit 16. As a result, the strength of the detection signal Vdet obtained in one detection operation increases, so that the sensor sensitivity can be improved.

In the detection device 1 of the present disclosure, the number of the partial detection areas PAA (optical sensors PD) included in each of the block units PAG1 and PAG2 can be changed. Thus, the resolution per inch (pixels per inch (ppi), hereinafter, referred to as "definition") can be set according to the information to be acquired.

For example, the number of the partial detection areas PAA (optical sensors PD) included in each of the block units PAG1 and PAG2 can be relatively reduced. This setting results in a longer detection time and a lower frame rate (for example, 20 frames per second (fps) or lower), the detection can be performed at a higher definition (for example, at 300 ppi or higher). Hereafter, the term "first mode" denotes a mode of performing the detection at a lower frame rate and a higher definition. By selecting the first mode of performing the detection at a lower frame rate and a higher definition, for example, a fingerprint on the surface of a finger can be acquired at a higher definition.

Alternatively, for example, the number of the partial detection areas PAA (optical sensors PD) included in each of the block units PAG1 and PAG2 can be relatively increased. This setting results in a lower definition (for example, 50 ppi or lower), the detection can be performed at a higher frame rate (for example, at 100 fps or higher) that allows the detection to be repeatedly performed in a shorter time in one frame. Hereafter, the term "second mode" denotes a mode of performing the detection at a higher frame rate and a lower definition. By selecting the second mode of performing the detection at a higher frame rate and a lower definition, for example, time-dependent changes in the pulse waves can be more accurately detected. In the second mode, calculation of a pulse wave velocity and calculation of blood pressure and the like are enabled by using the pulse waves acquired at a higher frame rate (for example, 1000 fps or higher).

For example, when acquiring the vascular image (vein pattern), the number of the partial detection areas PAA (optical sensors PD) included in each of the block units PAG1 and PAG2 is set to an intermediate value between those of the first mode and the second mode. This setting allows the detection to be performed at a medium frame rate higher than that of the first mode and lower than that of second mode (for example, higher than 20 fps and lower than 100 fps) and at a medium definition lower than that of the first mode and higher than that of the second mode (for example, higher than 50 ppi and lower than 300 ppi). Hereafter, the term "third mode" denotes a mode of performing the detection at a medium frame rate and a medium definition. The third mode of performing the detection at a medium frame rate and a medium definition is suitable for, for example, acquiring the vascular pattern of veins and the like.

As illustrated in FIG. 3, the reset circuit 17 includes a reference signal line Lvr, a reset signal line Lrst, and fourth switching elements TrR. The fourth switching elements TrR are provided correspondingly to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference signal COM to the reference signal line Lvr. This operation supplies the reference signal COM to a capacitive element Ca (refer to FIG. 4) included in each of the partial detection areas PAA.

Figure 4:
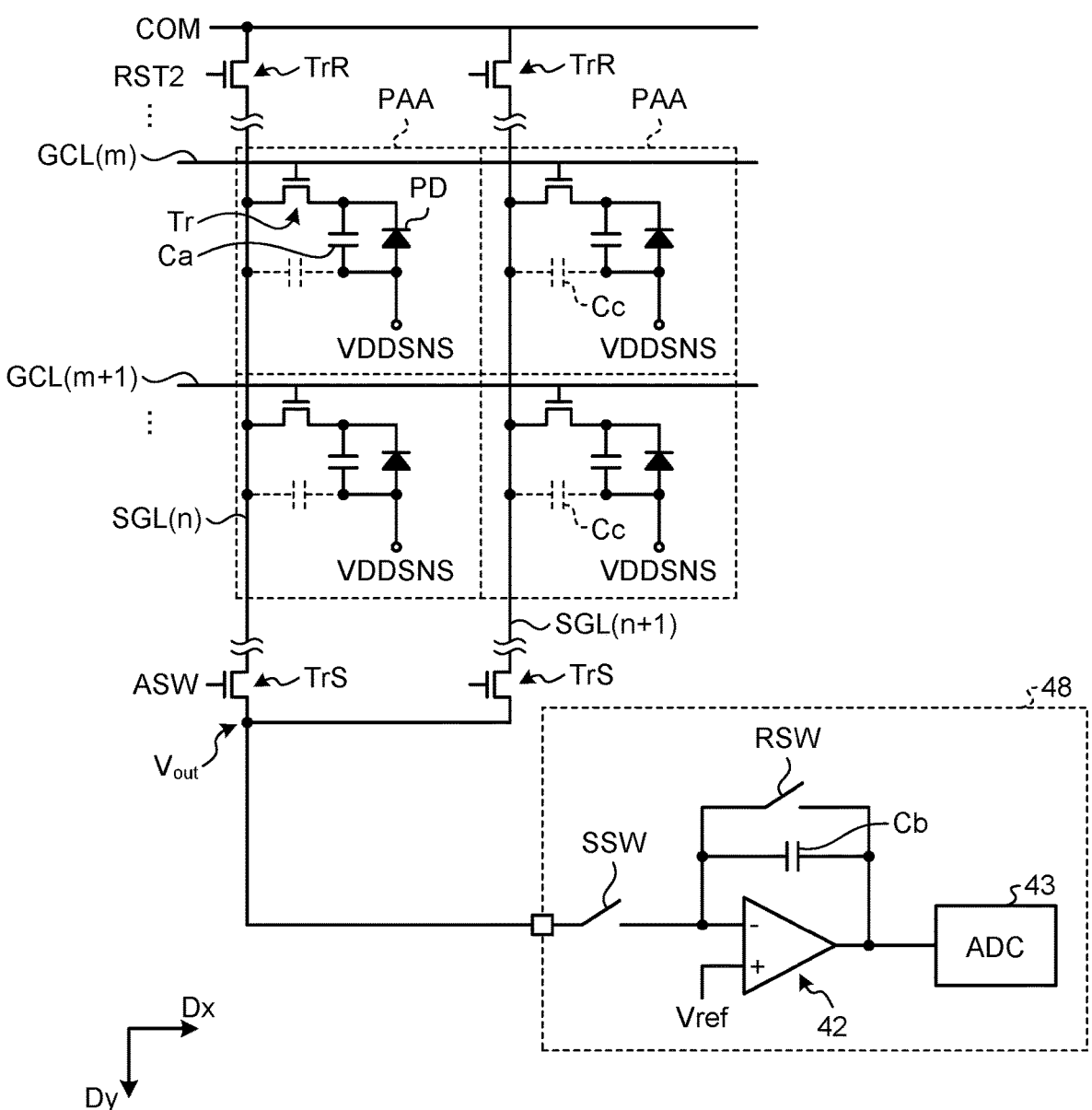
FIG. 4 is a circuit diagram illustrating a plurality of partial detection areas.

FIG. 4 is a circuit diagram illustrating the partial detection areas of the detection device according to the embodiment. FIG. 4 also illustrates a circuit configuration of the detection circuit 48. As illustrated in FIG. 4, each of the partial detection areas PAA includes the optical sensor PD, the capacitive element Ca, and a first switching element Tr1. The capacitive element Ca is a capacitor (sensor capacitance) generated in the optical sensor PD and is equivalently coupled in parallel with the optical sensor PD. In addition, signal line capacitance Cc is a parasitic capacitor (parasitic capacitance) generated on the signal line SGL and is equivalently provided between the signal line SGL and a node between the anode of the optical sensor PD and one end side of the capacitive element Ca.

FIG. 4 illustrates two gate lines GCL(m) and GCL(m+1) arranged in the second direction Dy among the gate lines GCL. FIG. 4 also illustrates two signal lines SGL(n) and SGL(n+1) arranged in the first direction Dx among the signal lines SGL. The partial detection area PAA is an area surrounded by the gate lines GCL and the signal lines SGL.

Each of the first switching elements Tr is provided correspondingly to the optical sensor PD. The first switching element Tr includes a thin-film transistor, and in this example, includes an n-channel metal oxide semiconductor (MOS) thin-film transistor (TFT).

The gates of the first switching elements Tr belonging to the partial detection areas PAA arranged in the first direction Dx are coupled to the gate line GCL. The sources of the first switching elements Tr belonging to the partial detection areas PAA arranged in the second direction Dy are coupled to the signal line SGL. The drain of the first switching element Tr is coupled to the cathode of the optical sensor PD and the capacitive element Ca.

The anode of the optical sensor PD is supplied with the sensor power supply potential VDDSNS from the power supply circuit 123. The signal line SGL and the capacitive element Ca are supplied with the reference signal COM that serves as an initial potential of the signal line SGL and the capacitive element Ca from the power supply circuit 123.

When the partial detection area PAA is irradiated with light, a current corresponding to the amount of the light flows through the optical sensor PD. As a result, an electric charge is stored in the capacitive element Ca. After the first switching element Tr is turned on, a current corresponding to the electric charge stored in the capacitive element Ca flows through the signal line SGL. The signal line SGL is coupled to the detection circuit 48 through a corresponding one of the third switching elements TrS of the signal line selection circuit 16. Thus, the detection device 1 can detect a signal corresponding to the amount of the light received by each optical sensor PD in each of the partial detection areas PAA or each of the block units PAG1 and PAG2.

During a read period Pdet (refer to FIG. 6), a switch SSW of the detection circuit 48 is turned on, and the detection circuit 48 is coupled to the signal lines SGL. The detection signal amplifier 42 of the detection circuit 48 converts a current supplied from the signal line SGL into a voltage corresponding to the value of the current and amplifies the result. A reference potential (Vref) having a fixed potential is supplied to a non-inverting input terminal (+) of the detection signal amplifier 42, and the signal lines SGL are coupled to an inverting input terminal (−) of the detection signal amplifier 42. In the embodiment, the same signal as the reference signal COM is supplied as the reference potential (Vref) voltage. The detection signal amplifier 42 includes a capacitive element Cb and a reset switch RSW. During a reset period Prst (refer to FIG. 6), the reset switch RSW is turned on, and the electric charge of the capacitive element Cb is reset.

Figure 5A:
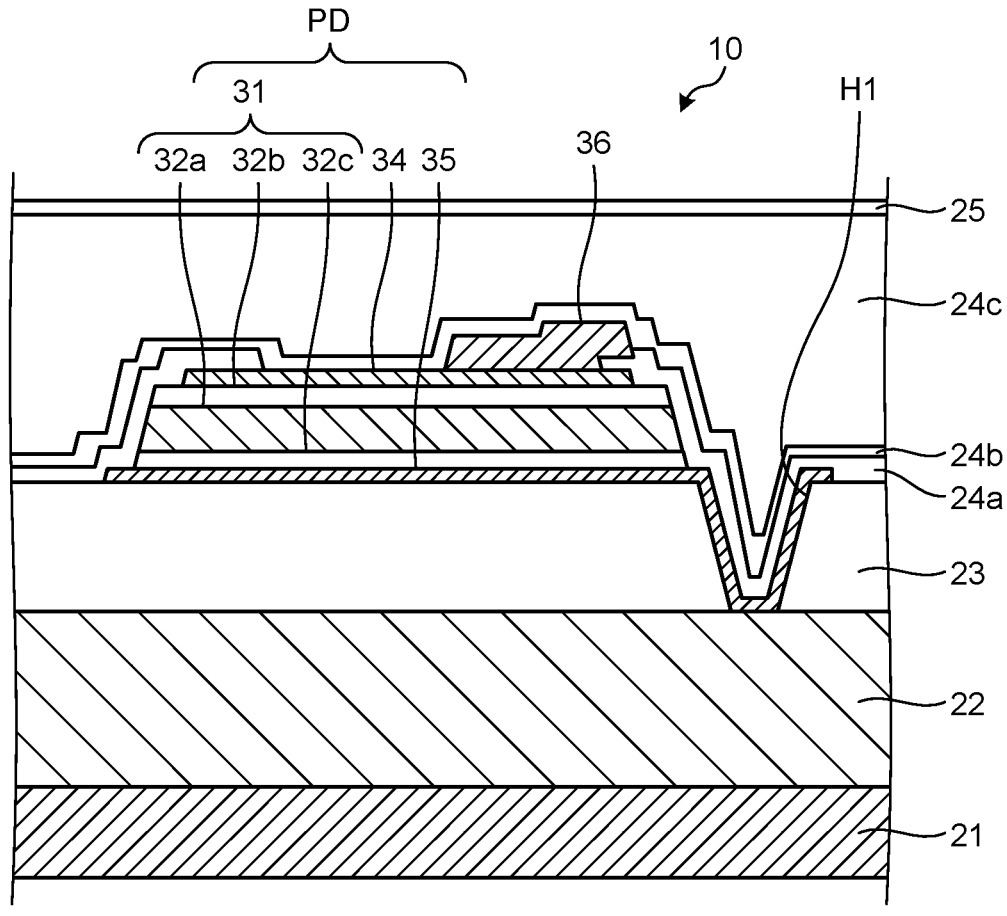
FIG. 5A is a sectional view illustrating a schematic sectional configuration of a sensor.

The following describes a configuration of the optical sensor PD. FIG. 5A is a sectional view illustrating a schematic sectional configuration of the sensor. As illustrated in FIG. 5A, the sensor 10 includes the sensor base member 21, a TFT layer 22, an insulating layer 23, the optical sensor PD, and insulating layers 24a, 24b, 24c, and 25. The sensor base member 21 is an insulating base member and is made using, for example, glass or a resin material. The sensor base member 21 is not limited to having a flat plate shape and may have a curved surface. In this case, the sensor base member 21 can be a film-like resin. The sensor base member 21 has a first surface and a second surface on the opposite side to the first surface. The TFT layer 22, the insulating layer 23, the optical sensor PD, and the insulating layers 24 and 25 are stacked in this order on the first surface.

The TFT layer 22 is provided with circuits such as the gate line drive circuit 15 and the signal line selection circuit 16 described above. The TFT layer 22 is also provided with TFTs, such as the first switching elements Tr, and various types of wiring, such as the gate lines GCL and the signal lines SGL. The sensor base member 21 and the TFT layer 22 serve as a drive circuit board that drives the sensor for each predetermined detection area and are also called a backplane or an array substrate.

The insulating layer 23 is an organic insulating layer and is provided on the TFT layer 22. The insulating layer 23 is a planarizing layer that planarizes asperities formed by the first switching elements Tr and various conductive layers formed in the TFT layer 22.

The optical sensor PD is provided on the insulating layer 23. The optical sensor PD includes a lower electrode 35, a semiconductor layer 31, and an upper electrode 34, which are stacked in this order.

The lower electrode 35 is provided above the insulating layer 23 and is electrically coupled to the first switching element Tr in the TFT layer 22 through a contact hole H1. The lower electrode 35 is the cathode of the optical sensor PD and is an electrode for reading the detection signal Vdet. A metal material such as molybdenum (Mo) or aluminum (Al) is used as the lower electrode 35. Alternatively, the lower electrode 35 may be a multilayered film formed by stacking these metal materials. The lower electrode 35 may be formed of, for example, a light-transmitting conductive material such as indium tin oxide (ITO).

The semiconductor layer 31 is formed of amorphous silicon (a-Si). The semiconductor layer 31 includes an i-type semiconductor layer 32a, a p-type semiconductor layer 32b, and an n-type semiconductor layer 32c. The i-type semiconductor layer 32a, the p-type semiconductor layer 32b, and the n-type semiconductor layer 32c constitute a specific example of a photoelectric conversion element. In FIG. 5A, the n-type semiconductor layer 32c, the i-type semiconductor layer 32a, and the p-type semiconductor layer 32b are stacked in this order in a direction orthogonal to a surface of the sensor base member 21. However, the semiconductor layer 31 may have a reversed configuration, that is, the p-type semiconductor layer 32b, the i-type semiconductor layer 32a, and the n-type semiconductor layer 32c may be stacked in this order. The semiconductor layer 31 may be a photoelectric conversion element formed of organic semiconductors.

The a-Si of the n-type semiconductor layer 32c is doped with impurities to form an n+ region. The a-Si of the p-type semiconductor layer 32b is doped with impurities to form a p+ region. The i-type semiconductor layer 32a is, for example, a non-doped intrinsic semiconductor and has lower conductivity than that of the p-type semiconductor layer 32b and the n-type semiconductor layer 32c.

The upper electrode 34 is the anode of the optical sensor PD and is an electrode for supplying the power supply potential VDDSNS to the photoelectric conversion layers. The upper electrode 34 is a light-transmitting conductive layer of, for example, ITO and is provided so as to be common to all the optical sensors PD.

The insulating layers 24a and 24b are provided on the insulating layer 23. The insulating layer 24a covers the periphery of the upper electrode 34 and is provided with an opening in a position overlapping the upper electrode 34. Coupling wiring 36 is coupled to the upper electrode 34 at a portion of the upper electrode 34 not provided with the insulating layer 24a. The insulating layer 24b is provided on the insulating layer 24a so as to cover the upper electrode 34 and the coupling wiring 36. The insulating layer 24c serving as a planarizing layer is provided on the insulating layer 24b. The insulating layer 25 is provided on the insulating layer 24c. However, the insulating layer 25 need not be provided.

Figure 5B:
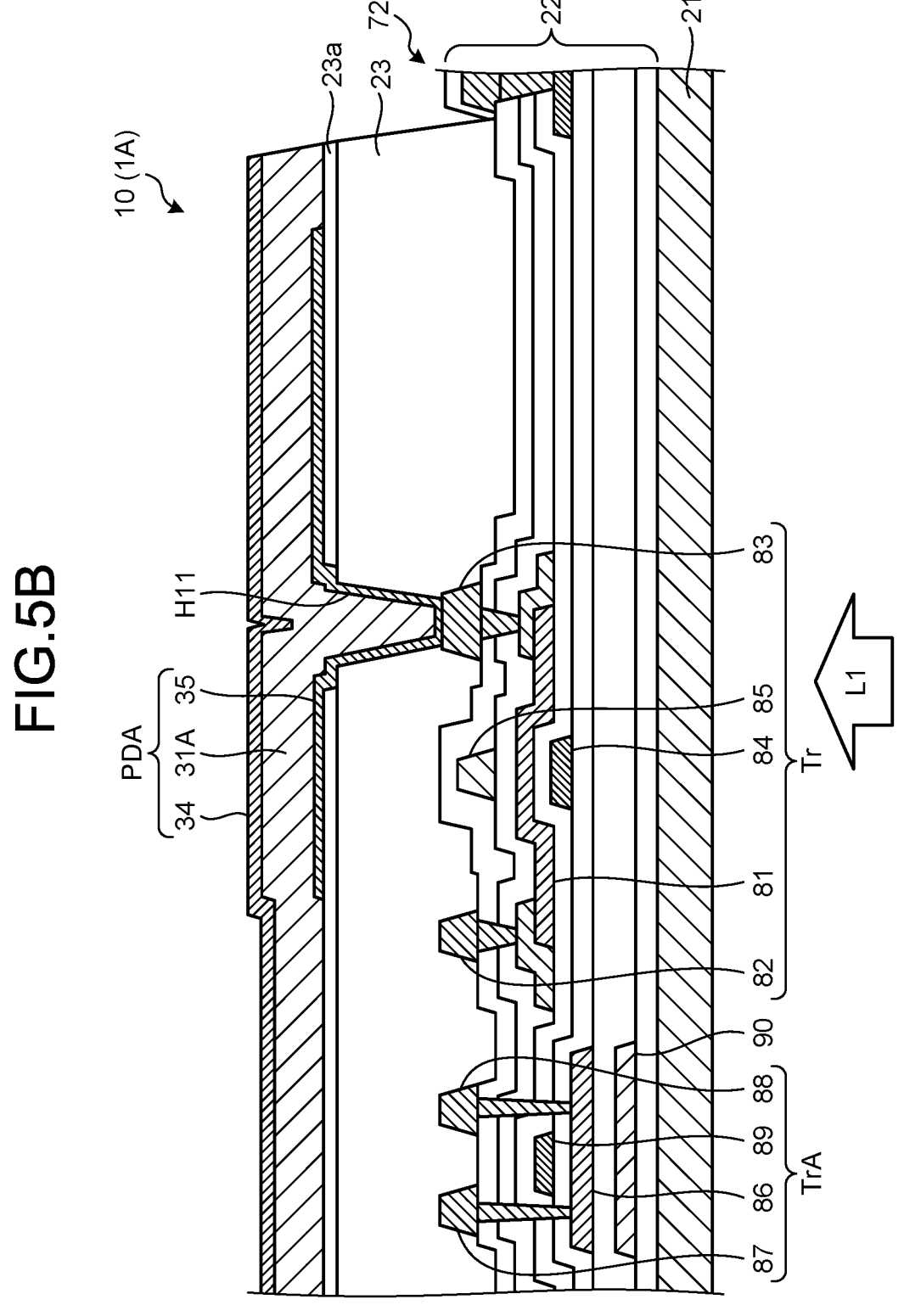
FIG. 5B is a sectional view illustrating a schematic sectional configuration of the sensor of a detection device according to a first modification.

FIG. 5B is a sectional view illustrating a schematic sectional configuration of the sensor of a detection device according to a first modification. As illustrated in FIG. 5B, in a detection device 1A of the first modification, an optical sensor PDA is provided above an insulating layer 23a. The insulating layer 23a is an inorganic insulating layer provided so as to cover the insulating layer 23 and is formed of, for example, silicon nitride (SiN). The optical sensor PDA includes a photoelectric conversion layer 31A, the lower electrode 35 (cathode electrode), and the upper electrode 34 (anode electrode). The lower electrode 35, the photoelectric conversion layer 31A, and the upper electrode 34 are stacked in this order in a direction orthogonal to a first surface S1 of the sensor base member 21.

The photoelectric conversion layer 31A changes in characteristics (for example, voltage-current characteristics and resistance value) depending on light emitted thereto. An organic material is used as a material of the photoelectric conversion layer 31A. Specifically, as the photoelectric conversion layer 31A, low-molecular-weight organic materials can be used, such as fullerene ($C_{60}$), phenyl-$C_{61}$-butyric acid methyl ester (PCBM), copper phthalocyanine (CuPc), fluorinated copper phthalocyanine ($F_{16}$CuPc), 5,6,11,12-tetraphenyltetracene (rubrene), and perylene diimide (PDI) (derivative of perylene).

The photoelectric conversion layer 31A can be formed by a vapor deposition process (dry process) using these low-molecular-weight organic materials. In this case, the photoelectric conversion layer 31A may be, for example, a multilayered film of CuPc and $F_{16}$CuPc, or a multilayered film of rubrene and $C_{60}$. The photoelectric conversion layer 31A can also be formed by a coating process (wet process). In this case, the photoelectric conversion layer 31A is made using a material obtained by combining one of the above-listed low-molecular-weight organic materials with a high-molecular-weight organic material. As the high-molecular-weight organic material, for example, poly(3-hexylthiophene) (P3HT) and F8-alt-benzothiadiazole (F8BT) can be used. The photoelectric conversion layer 31A can be a film made of a mixture of P3HT and PCBM, or a film made of a mixture of F8BT and PDI.

The lower electrode 35 faces the upper electrode 34 with the photoelectric conversion layer 31A interposed therebetween. For example, a light-transmitting conductive material such as ITO is used as the upper electrode 34. For example, a metal material such as silver (Ag) or aluminum (Al) is used as the lower electrode 35. Alternatively, the lower electrode 35 may be made of an alloy material containing at least one or more of these metal materials.

The lower electrode 35 can be formed as a light-transmitting transflective electrode by controlling the film thickness of the lower electrode 35. For example, the lower electrode 35 is formed of a thin Ag film having a thickness of 10 nm so as to have light transmittance of approximately 60%. In this case, the optical sensor PDA can detect light emitted from both sides of the sensor base member 21, for example, both light L1 emitted from the first surface Si side and light emitted from a second surface S2 side.

Although not illustrated in FIG. 5B, the insulating layer 24 may be provided so as to cover the upper electrode 34. The insulating layer is a passivation film and is provided to protect the optical sensor PDA.

As illustrated in FIG. 5B, the TFT layer 22 is provided with the first switching element Tr electrically coupled to the optical sensor PDA. The first switching element Tr includes a semiconductor layer 81, a source electrode 82, a drain electrode 83, and gate electrodes 84 and 85. The lower electrode 35 of the optical sensor PDA is electrically coupled to the drain electrode 83 of the first switching element Tr through a contact hole H11 provided in the insulating layers 23 and 23a.

The first switching element Tr has what is called a dual-gate structure provided with the gate electrodes 84 and 85 on the upper and lower sides of the semiconductor layer 81. However, the first switching element Tr is not limited to this structure and may have a top-gate structure or a bottom-gate structure.

FIG. 5B schematically illustrates a second switching element TrA and a terminal 72 that are provided in the peripheral area GA. The second switching element TrA is, for example, a switching element provided in the gate line drive circuit 15 (refer to FIG. 1). The second switching element TrA includes a semiconductor layer 86, a source electrode 87, a drain electrode 88, and a gate electrode 89. The second switching element TrA has what is called a top-gate structure provided with the gate electrode 89 on the upper side of the semiconductor layer 86. A light-blocking layer 90 is provided between the semiconductor layer 86 and the sensor base member 21 on the lower side of the semiconductor layer 86. The second switching element TrA is, however, not limited to this structure, and may have a bottom-gate structure or a dual-gate structure.

The semiconductor layer 81 of the first switching element Tr is provided in a layer different from that of the semiconductor layer 86 of the second switching element TrA. The semiconductor layer 81 of the first switching element Tr is formed of, for example, an oxide semiconductor. The semiconductor layer 86 of the second switching element TrA is formed of, for example, polysilicon.

Figure 6:
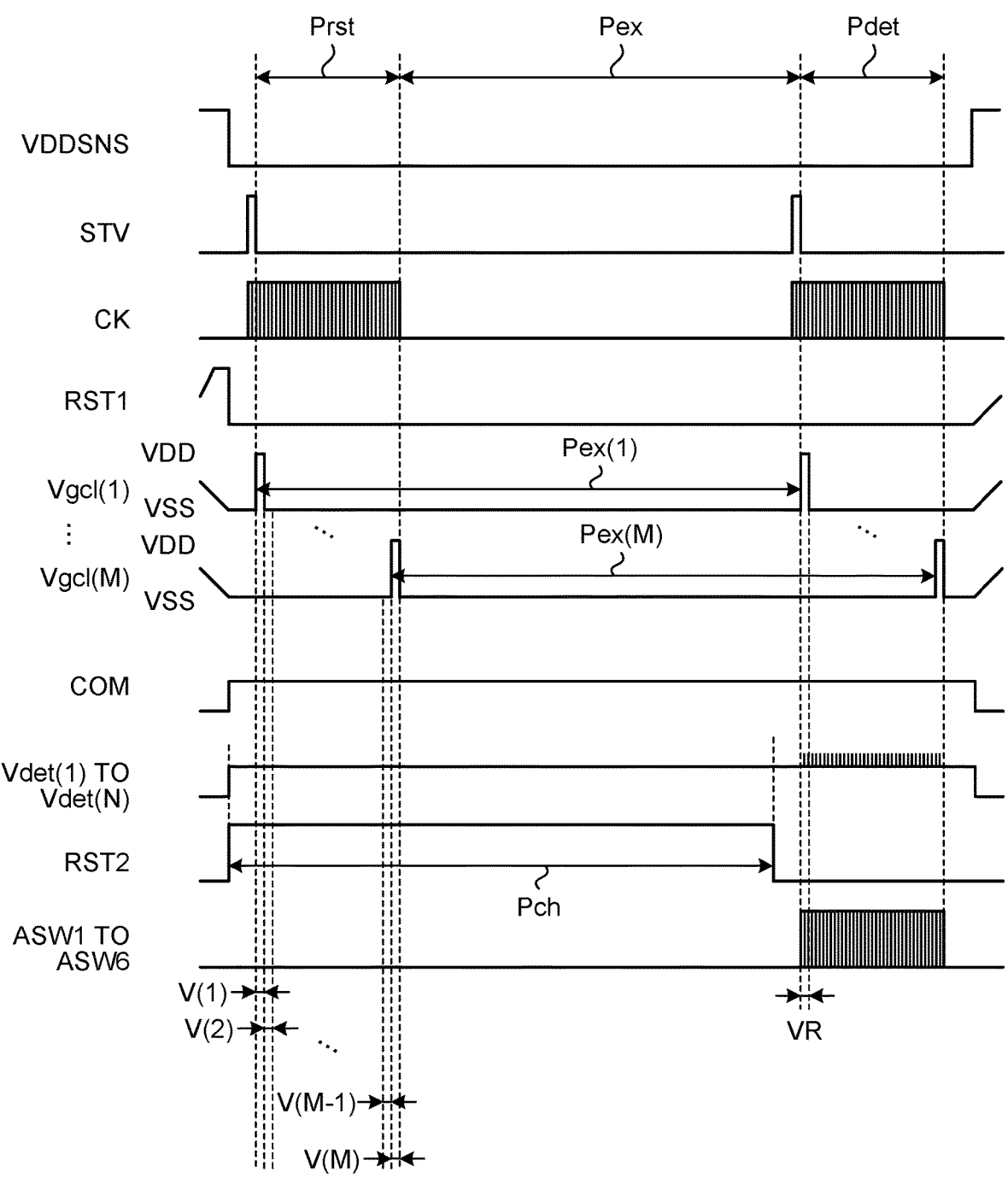
FIG. 6 is a timing waveform diagram illustrating an operation example of the detection device.
Figure 7:
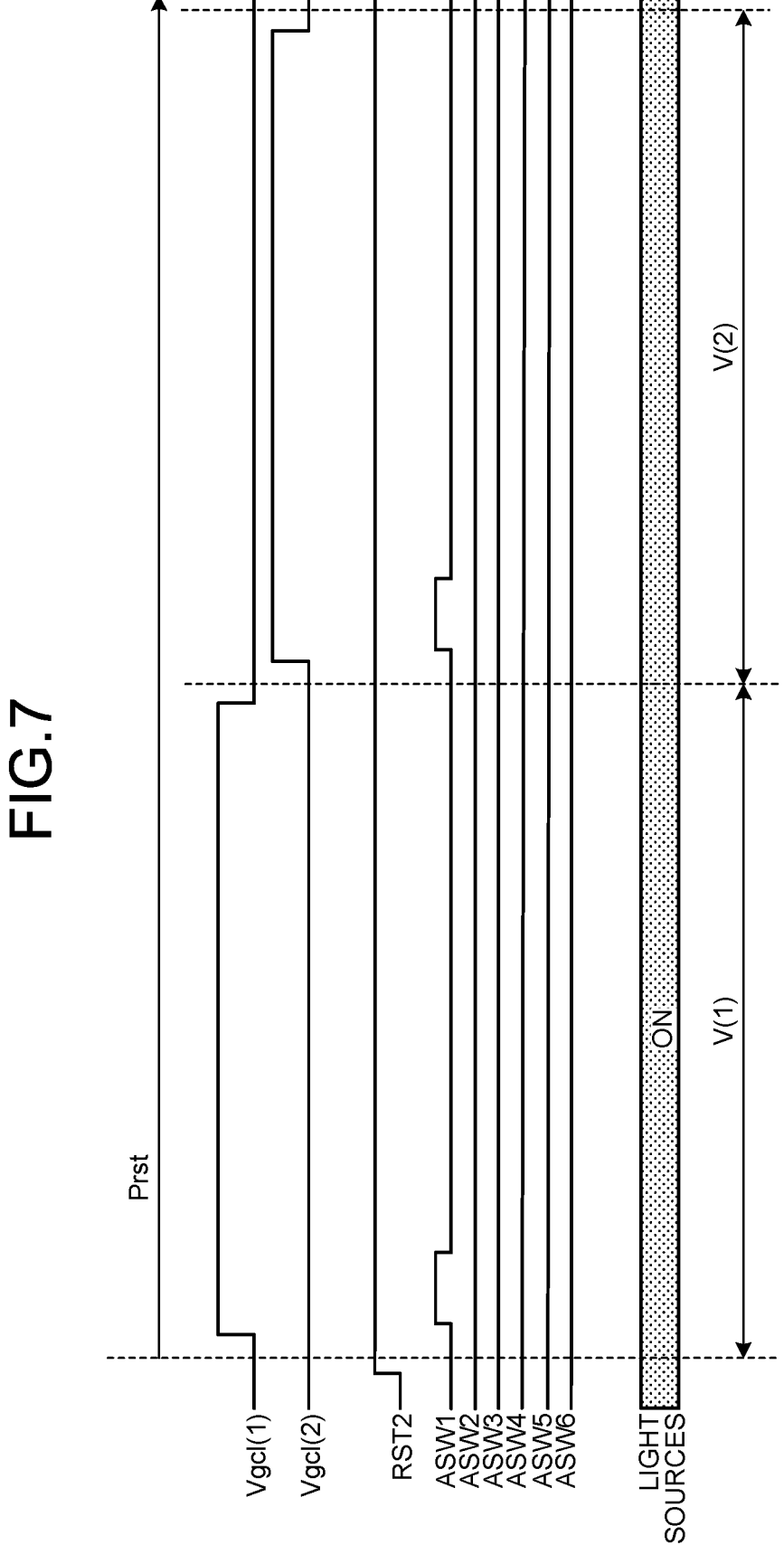
FIG. 7 is a timing waveform diagram illustrating an operation example during a reset period in FIG. 6.
Figure 8:
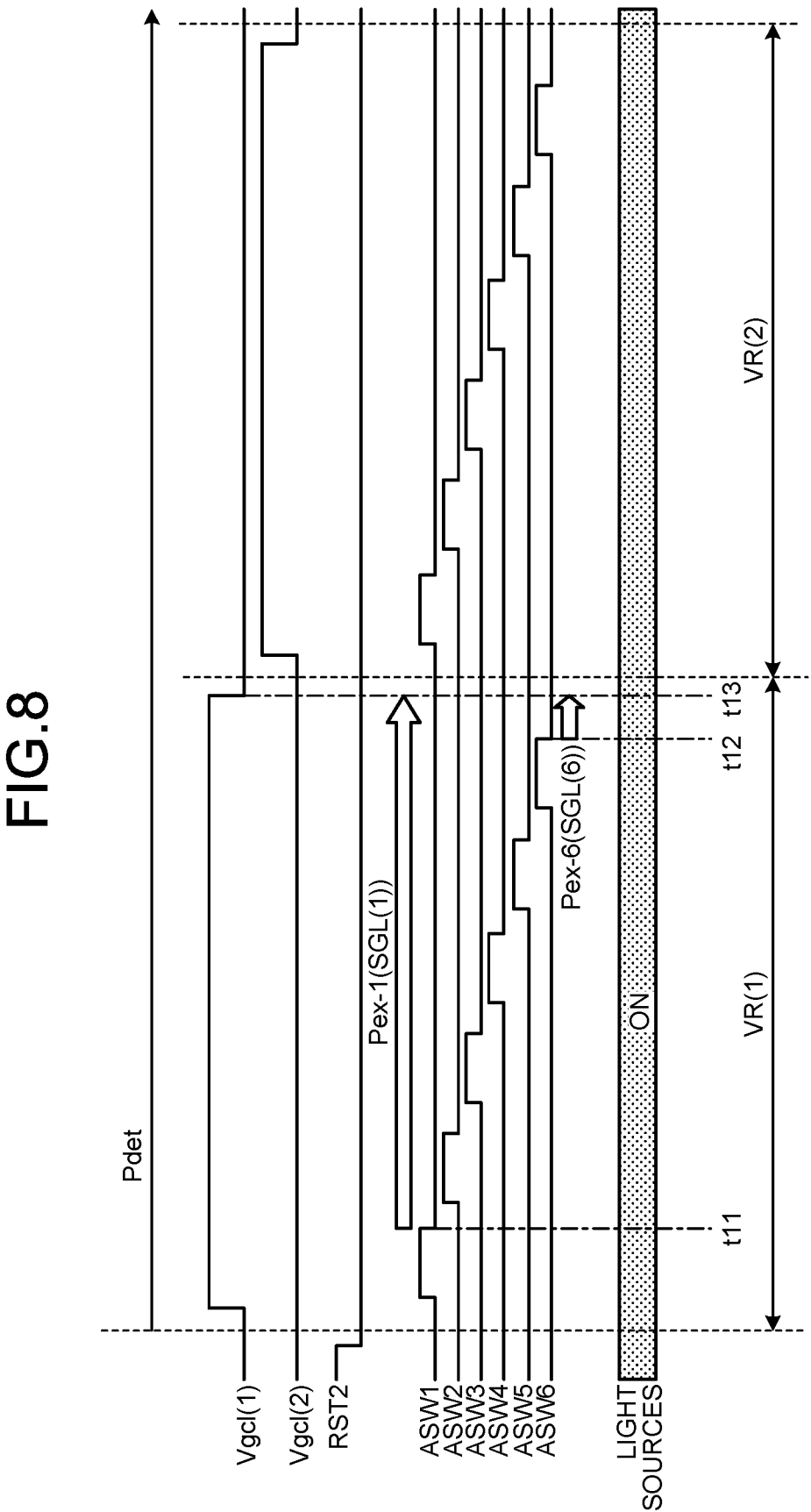
FIG. 8 is a timing waveform diagram illustrating an operation example during a read period in FIG. 6.
Figure 9:
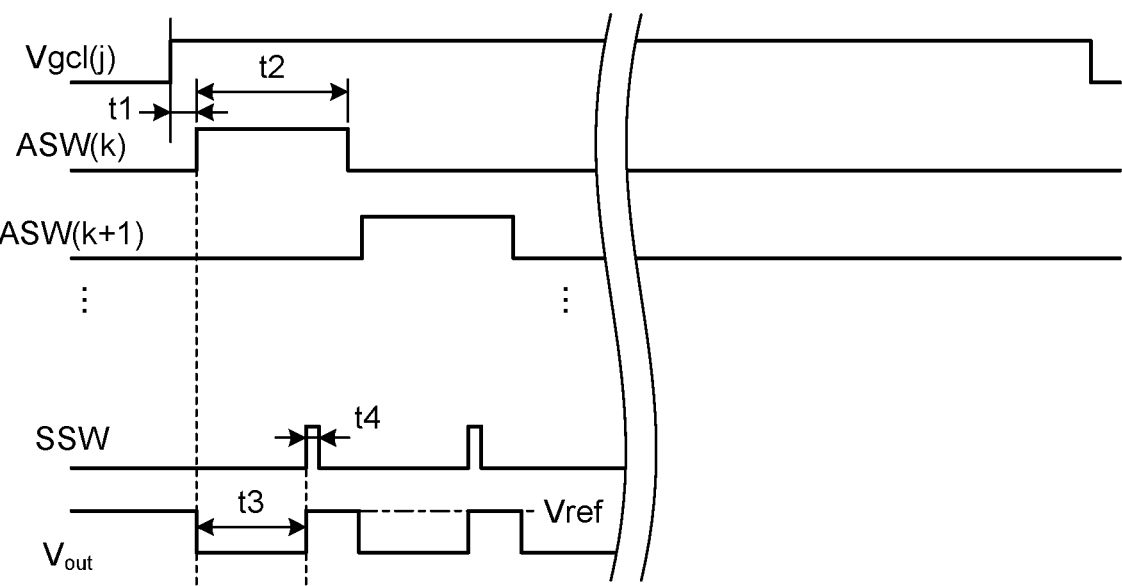
FIG. 9 is a timing waveform diagram illustrating an operation example during a drive period of one gate line included in the read period in FIG. 6.
Figure 10:
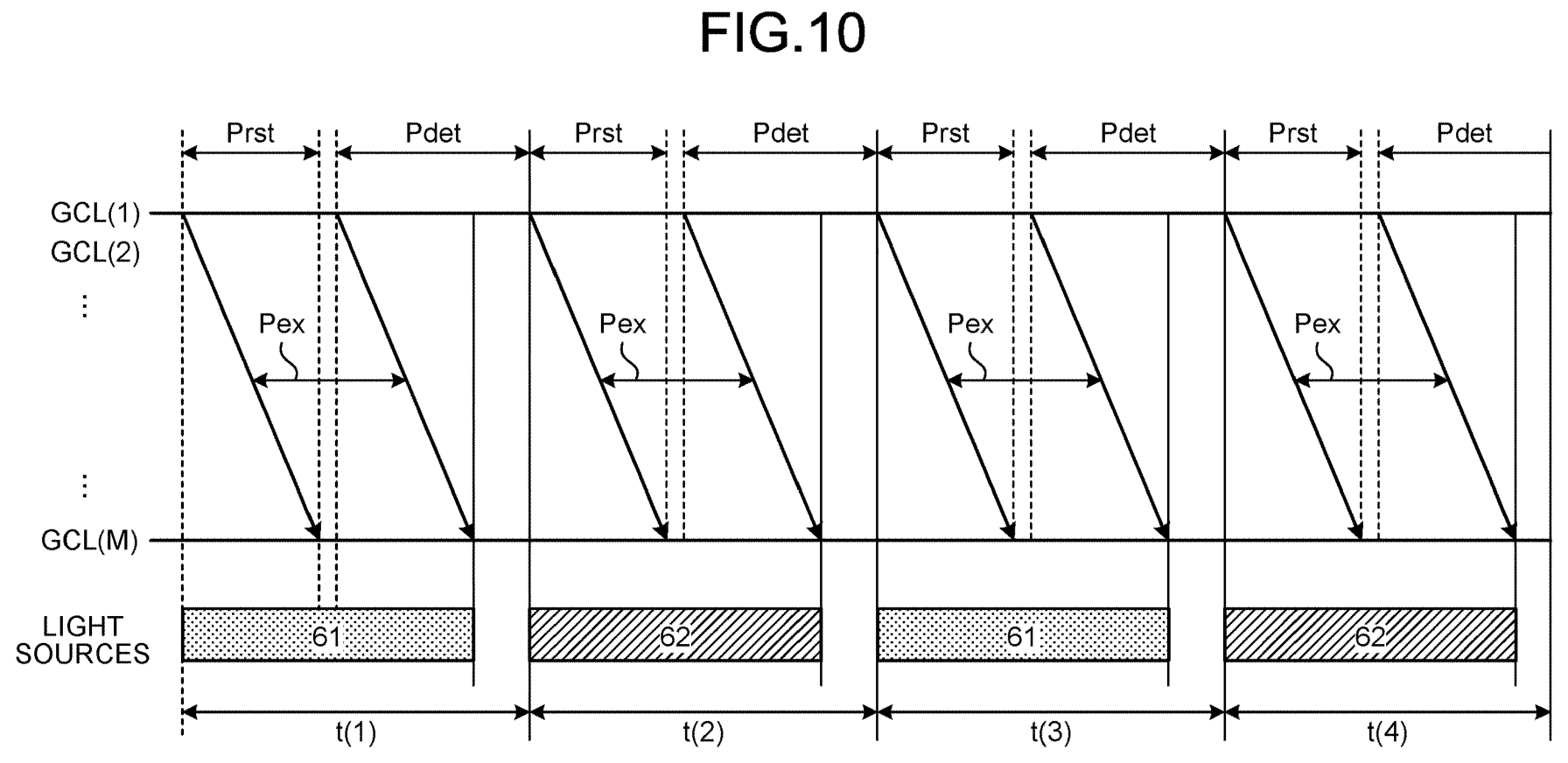

The following describes an operation example of the detection device 1. FIG. 6 is a timing waveform diagram illustrating the operation example of the detection device. FIG. 7 is a timing waveform diagram illustrating an operation example during the reset period in FIG. 6. FIG. 8 is a timing waveform diagram illustrating an operation example during the read period in FIG. 6. FIG. 9 is a timing waveform diagram illustrating an operation example during a drive period of one gate line included in a row read period VR in FIG. 6. FIG. 10 is an explanatory diagram for explaining a relation between driving of the sensor of the detection device and lighting operations of the light sources.

As illustrated in FIG. 6, the detection device 1 has the reset period Prst, an exposure period Pex, and the read period Pdet. The power supply circuit 123 supplies the sensor power supply potential VDDSNS to the anode of the optical sensor PD over the reset period Prst, the exposure period Pex, and the read period Pdet. The sensor power supply potential VDDSNS is a signal for applying a reverse bias between the anode and the cathode of the optical sensor PD. For example, the reference signal COM of substantially 0.75 V is applied to the cathode of the optical sensor PD, and the sensor power supply potential VDDSNS of substantially −1.25 V is applied to the anode thereof. As a result, a reverse bias of substantially 2.0 V is applied between the anode and the cathode. The control circuit 122 sets the reset signal RST2 to "H", and then, supplies the start signal STV and the clock signal CK to the gate line drive circuit 15 to start the reset period Prst. During the reset period Prst, the control circuit 122 supplies the reference signal COM to the reset circuit 17 and uses the reset signal RST2 to turn on the fourth switching elements TrR for supplying a reset voltage. This operation supplies the reference signal COM as the reset voltage to each of the signal lines SGL. The reference signal COM is set to, for example, 0.75 V.

During the reset period Prst, the gate line drive circuit 15 sequentially selects each of the gate lines GCL based on the start signal STV, the clock signal CK, and the reset signal RST1. The gate line drive circuit 15 sequentially supplies the gate drive signals Vgcl {Vgcl(1), . . . , Vgcl(M)} to the gate lines GCL. The gate drive signal Vgcl has a pulsed waveform having a power supply voltage VDD serving as a high-level voltage and a power supply voltage VSS serving as a low-level voltage. In FIG. 6, M gate lines GCL (where M is, for example, 256) are provided, and the gate drive signals Vgcl(1), . . . , Vgcl(M) are sequentially supplied to the respective gate lines GCL. Thus, the first switching elements Tr are sequentially brought into a conducting state and supplied with the reset voltage on a row-by-row basis. For example, a voltage of 0.75 V of the reference signal COM is supplied as the reset voltage.

Specifically, as illustrated in FIG. 7, the gate line drive circuit 15 supplies the gate drive signal Vgcl(1) at the high-level voltage (power supply voltage VDD) to the gate line GCL(1) during a period V(1). The control circuit 122 supplies any one of selection signals ASW1, ASW6 (selection signal ASW1 in FIG. 7) to the signal line selection circuit 16 during a period in which the gate drive signal Vgcl(1) is at the high-level voltage (power supply voltage VDD). This operation couples the signal line SGL of the partial detection area PAA selected by the gate drive signal Vgcl(1) to the detection circuit 48. As a result, the reset voltage (reference signal COM) is also supplied to coupling wiring between the third switching element TrS and the detection circuit 48.

In the same manner, the gate line drive circuit 15 supplies the gate drive signals Vgcl(2), . . . , Vgcl(M−1), Vgcl(M) at the high-level voltage to gate lines GCL(2), . . . , GCL(M−1), GCL(M) during periods V(2), . . . , V(M−1), V(M), respectively.

Thus, during the reset period Prst, the capacitive elements Ca of all the partial detection areas PAA are sequentially electrically coupled to the signal lines SGL and are supplied with the reference signal COM. As a result, the capacitance of the capacitive elements Ca is reset. The capacitance of the capacitive elements Ca of some of the partial detection areas PAA can be reset by partially selecting the gate lines and the signal lines SGL.

Examples of the method of controlling the exposure include a method of controlling the exposure during non-selection of the gate lines and a method of always controlling the exposure. In the method of controlling the exposure during non-selection of the gate lines, the gate drive signals {Vgcl(1), . . . , Vgcl(M)} are sequentially supplied to all the gate lines GCL coupled to the optical sensors PD serving as the detection targets, and all the optical sensors PD serving as the detection targets are supplied with the reset voltage. Then, after all the gate lines GCL coupled to the optical sensors PD serving as the detection targets are set to a low voltage (the first switching elements Tr are turned off), the exposure starts and the exposure is performed during the exposure period Pex. After the exposure ends, the gate drive signals {Vgcl(1), . . . , Vgcl(M)} are sequentially supplied to the gate lines GCL coupled to the optical sensors PD serving as the detection targets as described above, and reading is performed during the read period Pdet. In the method of always controlling the exposure, the control for performing the exposure can also be performed during the reset period Prst and the read period Pdet (the exposure is always controlled). In this case, the exposure period Pex(1) starts after the gate drive signal Vgcl(1) is supplied to the gate line GCL during the reset period Prst. The exposure periods Pex {(1), . . . , (M)} are periods during which the capacitive elements Ca are charged from the optical sensors PD. The electric charge stored in the capacitive element Ca during the reset period Prst causes a reverse directional current (from cathode to anode) to flow through the optical sensor PD due to light irradiation, and the potential difference in the capacitive element Ca decreases. The start timing and the end timing of the actual exposure periods Pex(1), . . . , Pex(M) are different among the partial detection areas PAA corresponding to the respective gate lines GCL. The "actual exposure period" is not a period during which the light source emits light but a period during which the electric charges corresponding to the light received by the optical sensors PD are stored in the respective capacitive elements Ca in the lighting period of the light source. Each of the exposure periods Pex(1), . . . , Pex(M) starts when the gate drive signal Vgcl changes from the power supply voltage VDD serving as the high-level voltage to the power supply voltage VSS serving as the low-level voltage during the reset period Prst. Each of the exposure periods Pex(1), . . . , Pex(M) ends when the gate drive signal Vgcl changes from the power supply voltage VSS to the power supply voltage VDD during the read period Pdet. The lengths of the exposure time of the exposure periods Pex(1), . . . , Pex(M) are equal.

During the exposure periods Pex {(1) . . . (M)}, a current corresponding to the light received by the optical sensor PD flows in each of the partial detection areas PAA. As a result, an electric charge is stored in each of the capacitive elements Ca.

At a time before the read period Pdet starts, the control circuit 122 sets the reset signal RST2 to a low-level voltage. This operation stops the operation of the reset circuit 17. The reset signal may be set to a high-level voltage only during the reset period Prst. During the read period Pdet, the gate line drive circuit 15 sequentially supplies the gate drive signals Vgcl(1) . . . , Vgcl(M) to the gate lines GCL in the same manner as during the reset period Prst.

Specifically, as illustrated in FIG. 8, the gate line drive circuit 15 supplies the gate drive signal Vgcl(1) at the high-level voltage (power supply voltage VDD) to the gate line GCL(1) during a row read period VR(1). The control circuit 122 sequentially supplies the selection signals ASW1, . . . , ASW6 to the signal line selection circuit 16 during a period in which the gate drive signal Vgcl(1) is at the high-level voltage (power supply voltage VDD). This operation sequentially or simultaneously couples the signal lines SGL of the partial detection areas PAA selected by the gate drive signal Vgcl(1) to the detection circuit 48. As a result, the detection signal Vdet for each of the partial detection areas PAA is supplied to the detection circuit 48.

In the same manner, the gate line drive circuit 15 supplies the gate drive signals Vgcl(2), . . . , Vgcl(M−1), Vgcl(M) at the high-level voltage to the gate lines GCL(2), . . . , GCL(M−1), GCL(M) during row read periods VR(2), . . . , VR(M−1), VR(M), respectively. That is, the gate line drive circuit 15 supplies the gate drive signal Vgcl to the gate line GCL during each of the row read periods VR(1), VR(2), . . . , VR(M−1), VR(M). The signal line selection circuit 16 sequentially selects each of the signal lines SGL based on the selection signal ASW in each period in which the gate drive signal Vgcl is set to the high-level voltage. The signal line selection circuit 16 sequentially couples each of the signal lines SGL to one detection circuit 48. Thus, the detection device 1 can output the detection signals Vdet of all the partial detection areas PAA to the detection circuit 48 during the read period Pdet.

With reference to FIG. 9, the following describes the operation example during the row read period VR that is a supply period of one of the gate drive signals Vgcl(j) in FIG. 6. In FIG. 6, the reference numeral of the row read period VR is assigned to the first gate drive signal Vgcl(1). The same applies to the other gate drive signals Vgcl(2) . . . , Vgcl(M). The index j is any one of the natural numbers 1 to M.

As illustrated in FIGS. 9 and 4, an output (Vout) of each of the third switching elements TrS has been reset to the reference potential (Vref) voltage in advance. The reference potential (Vref) voltage serves as the reset voltage and is set to, for example, 0.75 V. Then, the gate drive signal Vgcl(j) is set to a high level, and the first switching elements Tr of a corresponding row are turned on. Thus, each of the signal lines SGL in each row is set to a voltage corresponding to the electric charge stored in the capacitor (capacitive element Ca) of the partial detection area PAA. After a period t1 elapses from a rising edge of the gate drive signal Vgcl(j), a period t2 starts in which the selection signal ASW(k) is set to a high level. After the selection signal ASW(k) is set to the high level and the third switching element TrS is turned on, the electric charge stored in the capacitor (capacitive element Ca) of the partial detection area PAA coupled to the detection circuit 48 through the third switching element TrS changes the output (Vout) of the third switching element TrS (refer to FIG. 4) to a voltage corresponding to the electric charge stored in the capacitor (capacitive element Ca) of the partial detection area PAA (in a period t3). In the example of FIG. 9, this voltage is reduced from the reset voltage as illustrated in the period t3. Then, after the switch SSW is turned on (period t4 during which an SSW signal is set to a high level), the electric charge stored in the capacitor (capacitive element Ca) of the partial detection area PAA moves to the capacitor (capacitive element Cb) of the detection signal amplifier 42 of the detection circuit 48, and the output voltage of the detection signal amplifier 42 is set to a voltage corresponding to the electric charge stored in the capacitive element Cb. At this time, the potential of the inverting input portion of the detection signal amplifier 42 is set to an imaginary short-circuit potential of an operational amplifier, and therefore, becomes the reference potential (Vref). The A/D converter 43 reads the output voltage of the detection signal amplifier 42. In the example of FIG. 9, waveforms of the selection signals ASW(k), ASW(k+1), . . . corresponding to the signal lines SGL of the respective columns are set to a high level to sequentially turn on the third switching elements TrS, and the same operation is sequentially performed to sequentially read the electric charges stored in the capacitors (capacitive elements Ca) of the partial detection areas PAA coupled to the gate line GCL. ASW(k), ASW(k+1), . . . in FIG. 9 are, for example, any of ASW1 to ASW6 in FIG. 9.

Specifically, after the period t4 starts in which the switch SSW is on, the electric charge moves from the capacitor (capacitive element Ca) of the partial detection area PAA to the capacitor (capacitive element Cb) of the detection signal amplifier 42 of the detection circuit 48. At this time, the non-inverting input (+) of the detection signal amplifier 42 is set to the reference potential (Vref) voltage (for example, 0.75 V). As a result, the output (Vout) of the third switching element TrS is also set to the reference potential (Vref) voltage due to the imaginary short-circuit between input ends of the detection signal amplifier 42. The voltage of the capacitive element Cb is set to a voltage corresponding to the electric charge stored in the capacitor (capacitive element Ca) of the partial detection area PAA at a location where the third switching element TrS is turned on in response to the selection signal ASW(k). After the output (Vout) of the third switching element TrS is set to the reference potential (Vref) voltage due to the imaginary short-circuit, the output of the detection signal amplifier 42 reaches a voltage corresponding to the capacitance of the capacitive element Cb, and this output voltage is read by the A/D converter 43. The voltage of the capacitive element Cb is, for example, a voltage between two electrodes provided on a capacitor constituting the capacitive element Cb.

The period t1 is, for example, 20 μs. The period t2 is, for example, 60 μs. The period t3 is, for example, 44.7 μs. The period t4 is, for example, 0.98 μs.

As illustrated in FIG. 10, in each of a period t(1), a period t(2), a period t(3), and a period t(4), the detection device 1 performs the processing in the reset period Prst, the exposure periods Pex {(1), . . . , (M)}, and the read period Pdet described above. In the reset period Prst and the read period Pdet, the gate line drive circuit 15 sequentially scans the gate lines from GCL(1) to GCL(M). In the following description, the term "one-frame detection" denotes detection operation of one frame, that is, the detection in each period t. More specifically, "one-frame detection" denotes the detection in which the gate lines are scanned from GCL(1) to GCL(M) in the reset period Prst and the read period Pdet and the detection signals Vdet are acquired from the signal lines SGL in the respective columns.

The control circuit 122 can control the lighting and the non-lighting of the light sources according to the detection target. FIG. 10 illustrates an example in which the first light sources 61 are on during the periods t(1) and t(3), and the second light sources 62 are on during the periods t(2) and t(4). That is, in the example illustrated in FIG. 10, the control circuit 122 alternately switches between on and off of the first light sources 61 and the second light sources 62 for each one-frame detection. The present disclosure is not limited to this example. For example, the control circuit 122 may switch between on and off of the first light sources 61 and the second light sources 62 at intervals of a predetermined period of time, or may continuously turn on either of the first light sources 61 and the second light sources 62.

Although FIGS. 6 to 10 illustrate the example in which the gate line drive circuit 15 individually selects the gate line GCL, the present disclosure is not limited to this example. The gate line drive circuit 15 may simultaneously select a predetermined number (two or more) of the gate lines GCL and sequentially supply the gate drive signals Vgcl to the gate lines GCL in units of the predetermined number of the gate lines GCL. The signal line selection circuit 16 may also simultaneously couple a predetermined number (two or more) of the signal lines SGL to one detection circuit 48. Moreover, the gate line drive circuit 15 may scan some of the gate lines GCL while skipping the others.

As illustrated in FIG. 8, in the row read period VR(1), the selection signals ASW1, . . . , ASW6 are sequentially supplied to the signal line selection circuit 16 during the period in which the gate drive signal Vgcl(1) is at the high-level voltage (power supply voltage VDD). That is, even after the selection signal ASW1 is set to a low-level voltage at time t11, the exposure continues during an exposure period Pex-1 until the gate drive signal Vgcl(1) is set to the low-level voltage at time t13. The signal line SGL(1) corresponding to the selection signal ASW1 is charged with an electric charge corresponding to the exposure period Pex-1 from the optical sensor PD.

In the same manner, each of the signal lines SGL is charged with an electric charge during a corresponding one of exposure periods Pex-1, . . . , Pex-6 corresponding to the selection signals ASW1, . . . , ASW6. For example, the exposure period Pex-6 is a period after the selection signal ASW6 is set to the low-level voltage at time t12 until the gate drive signal Vgcl(1) is set to the low-level voltage at time t13, and the exposure period Pex differs column by column.

In the next row read period VR(2), the detection circuit 48 is supplied with a signal obtained by adding an electric charge that has been charged in the exposure periods Pex-1(SGL(1)), . . . , Pex-6(SGL(6)) of the previous row read period VR(1) to the detection signal Vdet of the second row.

As described above, the detection device 1 has the configuration including, for example, a plurality of types of light sources (first light sources 61 and second light sources 62) that emit light having different wave lengths, and thereby, can acquire a fingerprint acquired by detecting the light reflected on the surface of a finger of the subject and the various types of biometric information acquired by detecting the light reflected in or transmitted through the finger or the wrist of the subject.

Figure 11:
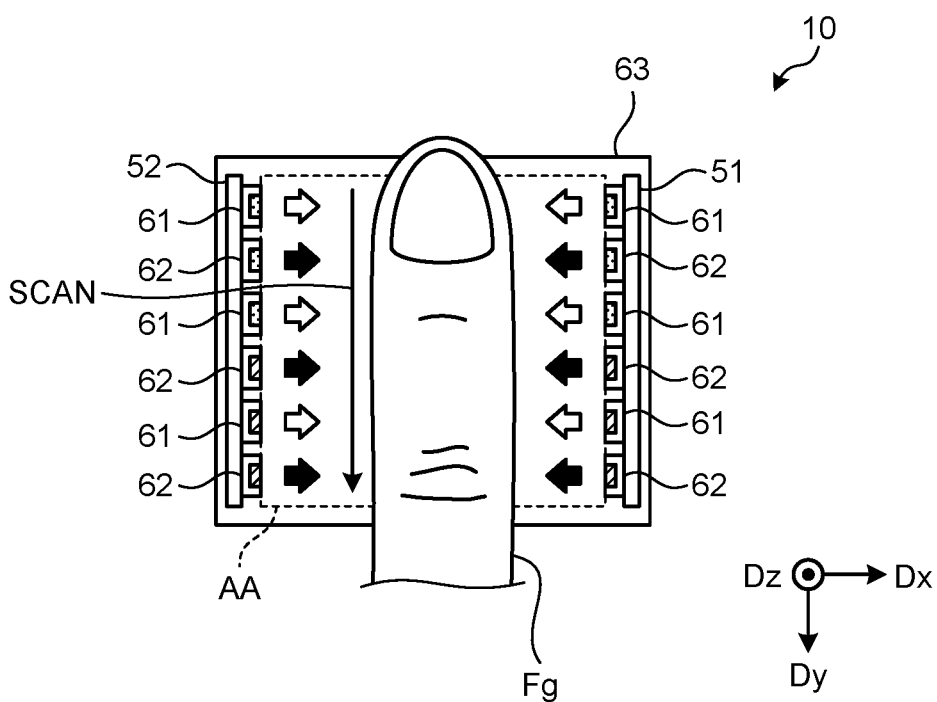
FIG. 11 is a plan view schematically illustrating a relation between the sensor, first light sources, and second light sources in the detection device according to the embodiment.

As a specific example of the information on the living body acquired by the detection device 1, the following describes an example of acquiring the pulse waves serving as biometric information for calculating an oxygen saturation level in the blood (hereinafter, called "blood oxygen saturation level" (SpO$_2$)). FIG. 11 is a plan view schematically illustrating a relation between the sensor, the first light sources, and the second light sources in the detection device according to the embodiment.

As illustrated in FIG. 11, the detection device 1 includes a filter 63. The filter 63 is disposed so as to overlap the detection area AA from one end to the other end in a scan direction SCAN of the sensor 10. The filter 63 has a transmission bandwidth for transmitting the first light emitted from the first light sources 61 and the second light emitted from the second light sources 62. In a configuration according to the embodiment, the filter 63 is not required, and the configuration may exclude the filter 63.

In the configuration illustrated in FIG. 11, the scan direction SCAN is the direction in which the gate line drive circuit 15 scans the gate line GCL. That is, one gate line GCL is provided so as to extend in the first direction Dx in the detection area AA and is coupled to the partial detection areas PAA provided in the detection area AA. One signal line SGL is provided so as to extend in the second direction Dy in the detection area AA and is coupled to the optical sensors PD in the detection area AA.

The first light source base member 51 and the second light source base member 52 face each other in the first direction Dx with the detection area AA interposed therebetween in the plan view. The first and the second light sources 61 and 62 are provided on a surface of the first light source base member 51 facing the second light source base member 52. The first and the second light sources 61 and 62 are also provided on a surface of the second light source base member 52 facing the first light source base member 51. The first and the second light sources 61 and 62 are arranged in the first direction Dx along the periphery of the detection area AA and are alternately provided in the second direction Dy on each of the first light source base member 51 and the second light source base member 52.

The first light sources 61 emit the first light in a direction parallel to the first direction Dx. As a result, the detection area AA is irradiated by the first light. The second light sources 62 emit the second light in the direction parallel to the first direction Dx. As a result, the detection area AA is irradiated by the second light.

Figure 12:
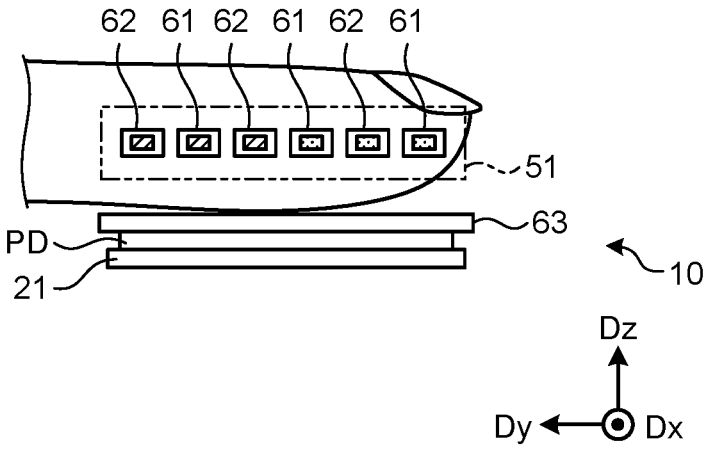
FIG. 12 is a side view of the detection device illustrated in FIG. 11 as viewed in a first direction Dx.

FIG. 12 is a side view of the detection device illustrated in FIG. 11 as viewed in the first direction Dx. As illustrated in FIG. 12, the object to be detected such as the finger Fg or the wrist of the subject comes in contact with or in proximity to the top of the sensor 10 with the filter 63 interposed therebetween. The first and the second light sources 61 and 62 are arranged above the sensor 10 and the filter 63 and are arranged with the object to be detected such as the finger Fg or the wrist of the subject interposed therebetween in the first direction Dx.

In this example, visible light in red (red light) having a wavelength of from 600 nm to 700 nm, specifically, approximately 660 nm is employed as the first light emitted from the first light sources 61, and infrared light having a wavelength of from 780 nm to 950 nm, specifically, approximately 850 nm is employed as the second light emitted from the second light sources 62. In the case of acquiring the human blood oxygen saturation level ($SpO_2$), a pulse wave acquired using the first light (red light) and a pulse wave acquired using the second light (infrared light) are used.

Since the amount of light absorbed by hemoglobin changes with the amount of oxygen absorbed by the hemoglobin, the optical sensor PD detects the amount of light obtained by subtracting the amount of the light absorbed by blood (hemoglobin) from the amount of the emitted first and second light. Most of the blood oxygen is reversibly bound to hemoglobin in red blood cells, and a small fraction of the blood oxygen is dissolved in blood plasma. More specifically, the value of what percentage of the allowable amount of oxygen is bound to the blood as a whole is called "oxygen saturation level" ($SpO_2$). The blood oxygen saturation level can be calculated from the amount obtained by subtracting the amount of the light absorbed by the blood (hemoglobin) from the amount of the light emitted at the two wavelengths of the first light and the second light.

The oxygen saturation level ($SpO_2$) is determined by the ratio of hemoglobin in blood bound to oxygen (oxygenated hemoglobin (O2Hb)) to hemoglobin in blood not bound to oxygen (reduced hemoglobin (HHb). The light absorption characteristics of red light are represented as HHb>>O2Hb, indicating that HHb has significantly larger absorbance, while the light absorption characteristics of infrared light are represented as HHb≈O2Hb, indicating that O2Hb has slightly larger absorbance.

The first light emitted from the first light sources 61 travels in the direction parallel to the first direction Dx and enters the finger Fg or the wrist of the subject. The first light emitted from the first light sources 61 penetrates into the living body and is reflected in the finger Fg or the wrist of the subject. The reflected light reflected in the finger Fg or the wrist of the subject travels in the third direction Dz and enters the detection area AA of the sensor 10 through the filter 63.

The second light emitted from the second light sources 62 travels in the direction parallel to the first direction Dx and enters the finger Fg or the wrist of the subject. The second light emitted from the second light sources 62 penetrates into the living body and is reflected in the finger Fg or the wrist of the subject. The reflected light reflected in the finger Fg or the wrist of the subject travels in the third direction Dz and enters the detection area AA of the sensor 10 through the filter 63.

The arrangement of the first and the second light sources 61 and 62 is not limited to the example illustrated in FIGS. 11 and 12. For example, the first and the second light may be emitted from above the object to be detected such as the finger Fg or the wrist of the subject illustrated in FIG. 12, specifically, in the third direction Dz. Alternatively, the first and the second light sources 61 and 62 may be, for example, what are called direct-type light sources provided directly below the detection area AA.

In the example illustrated in FIG. 10, the reset period Prst, the exposure period Pex, and the read period Pdet are provided in the one-frame detection in each of the periods t(1), t(2), t(3), and t(4). In the reset period Prst and the read period Pdet, the gate line drive circuit 15 sequentially scans the gate lines from GCL(1) to GCL(M).

As illustrated in FIG. 10, in the one-frame detection in the period t(1), the control circuit 122 (detection controller 11) controls the first light sources 61 to be on and the second light sources 62 to be off during the exposure period Pex. In the one-frame detection in the period t(2), the control circuit 122 (detection controller 11) controls the first light sources 61 to be off and the second light sources 62 to be on during the exposure period Pex. In the same manner, the first light sources 61 are controlled to be on and the second light sources 62 are controlled to be off during the exposure period Pex in the one-frame detection in the period t(3), and the first light sources 61 are controlled to be off and the second light sources 62 are controlled to be on during the exposure period Pex in the one-frame detection in the period t(4).

Thus, the first and the second light sources 61 and 62 are controlled to be on and off in a time-division manner for each one-frame detection. With this control, a first detection signal detected by the optical sensor PD based on the first light and a second detection signal detected by the optical sensor PD based on the second light are output to the detection circuit 48 in a time-division manner.

Since the calculation of the blood oxygen saturation level ($SpO_2$) uses the pulse wave acquired using the first light and the pulse wave acquired using the second light, the gap in detection timing between the first detection signal detected based on the first light and the second detection signal detected based on the second light is preferably smaller. The following describes an operation example that can reduce the gap in detection timing between the first detection signal detected based on the first light and the second detection signal detected based on the second light, with reference to FIGS. 13 and 14.

Figure 13:
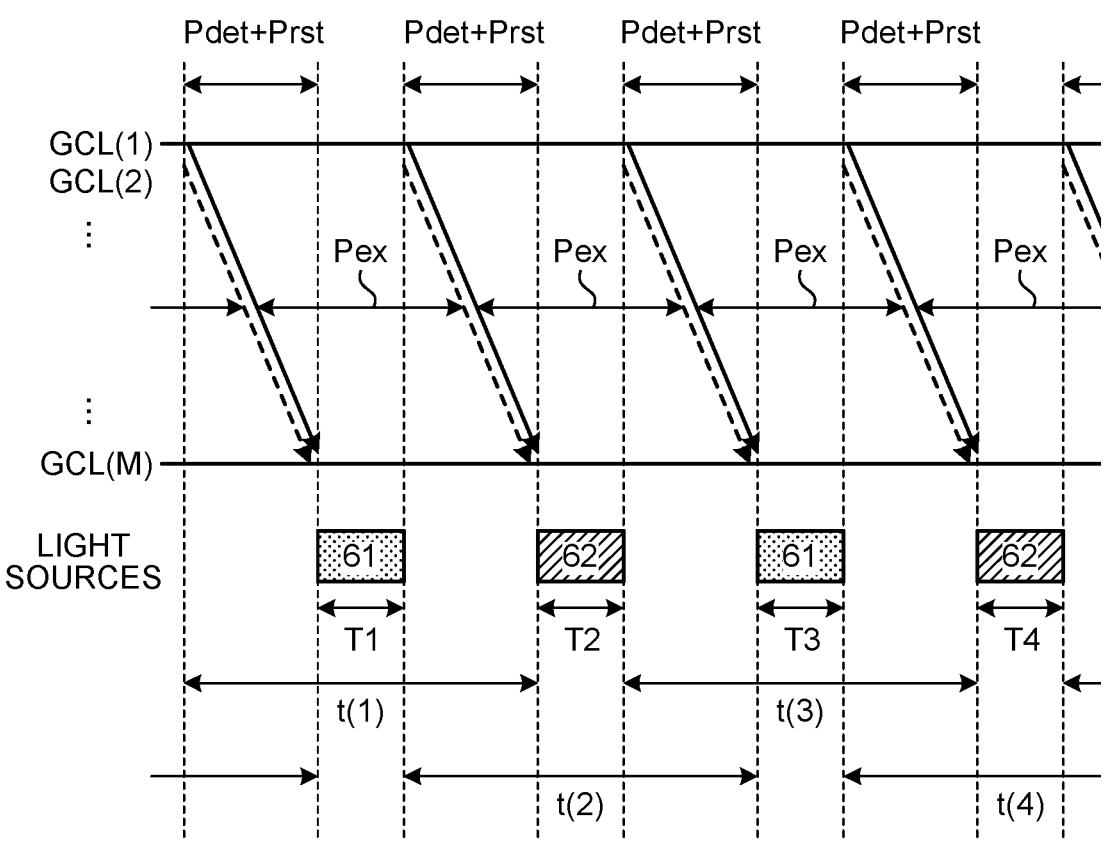
FIG. 13 is an explanatory diagram for explaining an operation example of the detection device according to the embodiment.
Figure 14:
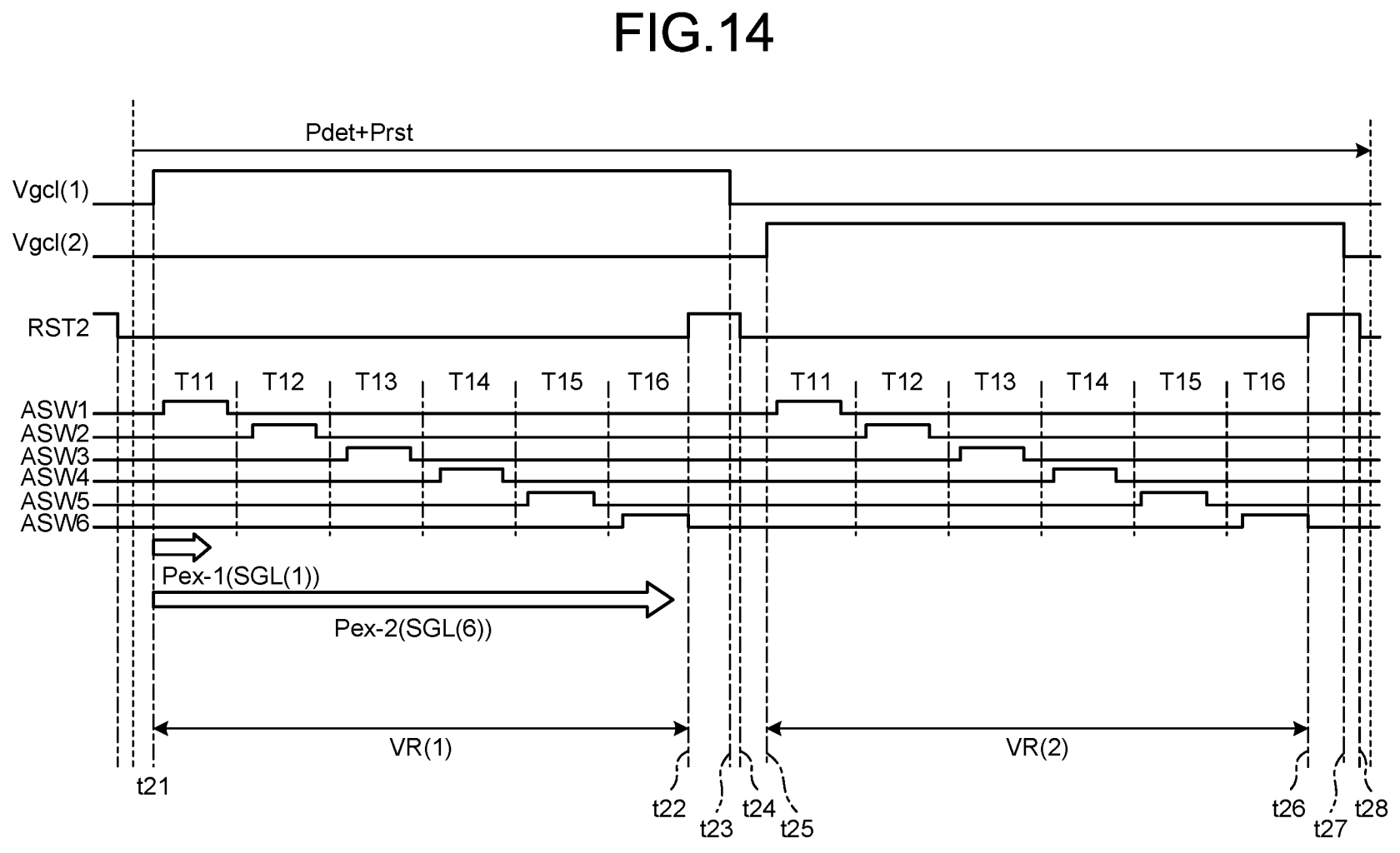

FIG. 13 is an explanatory diagram for explaining the operation example of the detection device according to the embodiment. FIG. 14 is a timing waveform diagram illustrating the operation example of the detection device according to the embodiment. The example illustrated in FIG. 13 indicates the reset period Prst with a solid arrow and the read period Pdet with a dashed arrow for each of the periods t(1), t(2), t(3), and t(4).

In the operation example illustrated in FIG. 13, the reset period Prst of the period t(1) provided with a period T1 to turn on the first light sources 61 is executed in parallel with the read period Pdet of the previous frame. The reset period Prst of the period t(2) provided with a period T2 to turn on the second light sources 62 is executed in parallel with the read period Pdet of the previous frame. Subsequently, in the same manner, the reset period Prst of the period t(3) provided with a period T3 to turn on the first light sources 61 is executed in parallel with the read period Pdet of the previous frame, and the reset period Prst of the period t(4) provided with a period T4 to turn on the second light sources 62 is executed in parallel with the read period Pdet of the previous frame. Specifically, for example, immediately after each row of the frame for the period t(1) is read, the row of the frame for the period t(2) is reset and irradiated with light during the period T2. Then, immediately after each row of the frame for the period t(2) is read, the row of the frame for the period t(3) is reset and irradiated with light during the period T3. Subsequently, the same operation is repeated. This operation reduces the gap in detection timing between the detection based on the first light emitted from the first light sources 61 and the detection based on the first light emitted from the second light sources 62 in each row.

In the operation example illustrated in FIG. 13, the gate drive signal Vgcl is supplied to the gate lines GCL row by row, and the first switching elements Tr belonging to a certain row are brought into a coupled state. Specifically, as illustrated in FIG. 14, the gate line drive circuit 15 supplies the gate drive signal Vgcl(1) at the high-level voltage (power supply voltage VDD) to the gate line GCL(1) at time t21. The row read period VR(1) starts at time t21 when the gate drive signal Vgcl(1) is set to the high-level voltage.

Specifically, the control circuit 122 sequentially supplies the selection signals ASW1, . . . , ASW6 to the signal line selection circuit 16 during a period in which the gate drive signal Vgcl(1) is at the high-level voltage (power supply voltage VDD). The third switching elements TrS are sequentially brought into the coupled state in response to the selection signals ASW1, . . . , ASW6. That is, during the period of reading each row (row read period VR(1)), when the first switching elements Tr of the certain row are in the coupled state, the signal line selection circuit 16 couples the signal lines SGL to the detection circuit 48 column by column in a predetermined order. As a result, the detection signal Vdet for each of the partial detection areas PAA is supplied to the detection circuit 48.

In FIG. 14, the selection signals ASW1, . . . , ASW6 are supplied in the order of periods T11, . . . , T16 in a time-division manner. At time t22, the control circuit 122 sets the selection signal ASW6 to the low-level voltage, and the reading of the last column ends. That is, the row read period VR(1) ends when the gate drive signal Vgcl(1) is at the high-level voltage and the selection signal ASW6 has changed to the low-level voltage.

After the completion of the read period of the certain row (row read period VR(1)) and before the start of the read period of a row next to the certain row (row read period VR(2)), a reset potential (reference signal COM) is supplied to the optical sensors PD and the signal lines SGL belonging to the certain row. Specifically, the control circuit 122 supplies the reset signal RST2 to the reset signal line Lrst at time t22. This operation turns on the fourth switching elements TrR to supply the reference signal COM to the optical sensors PD and the signal lines SGL corresponding to the gate line GCL(1).

In the example illustrated in FIG. 14, at time t22, the time when the reset signal RST2 is set to the high-level voltage coincides with the time when the selection signal ASW6 is set to the low-level voltage. However, the timing is not limited thereto. The reset signal RST2 may be set to the high-level voltage after a predetermined period of time has elapsed since the selection signal ASW6 has been set to the low-level voltage.

Then, at time t23, the gate line drive circuit 15 sets the gate drive signal Vgcl(1) to the low-level voltage. This operation brings the first switching elements Tr of the certain row into a non-coupled state. At time t24, the control circuit 122 sets the reset signal RST2 to the low-level voltage. This operation ends the read period Pdet and reset period Prst of the first row.

Then, at time t25, the gate line drive circuit 15 supplies the gate drive signal Vgcl(2) at the high-level voltage (power supply voltage VDD) to the gate line GCL(2) of the second row. Subsequently, in the same manner as in the first row, the read period Pdet and the reset period Prst of the second row are executed from time t26 to time t28. The one-frame detection can be performed by repeating this operation to the last row (gate line GCL(256)).

During the periods T1, T2, T3, and T4 (refer to FIG. 13) in which the light sources are turned on, none of the gate lines GCL is selected (the gate drive signals Vgcl are at the low-level voltage). That is, the light sources are off during the row read period VR in which the first switching elements Tr in the certain row are in the coupled state, and the light sources are on during the periods T1, T2, T3, and T4 in which all the first switching elements Tr are in the non-coupled state.

As described above, in the example illustrated in FIGS. 13 and 14, the read period Pdet and the reset period Prst in the detection operations of two consecutive frames are executed in parallel. This can reduce the gap in detection timing between the first detection signal detected based on the first light and the second detection signal detected based on the second light.

Figure 15:
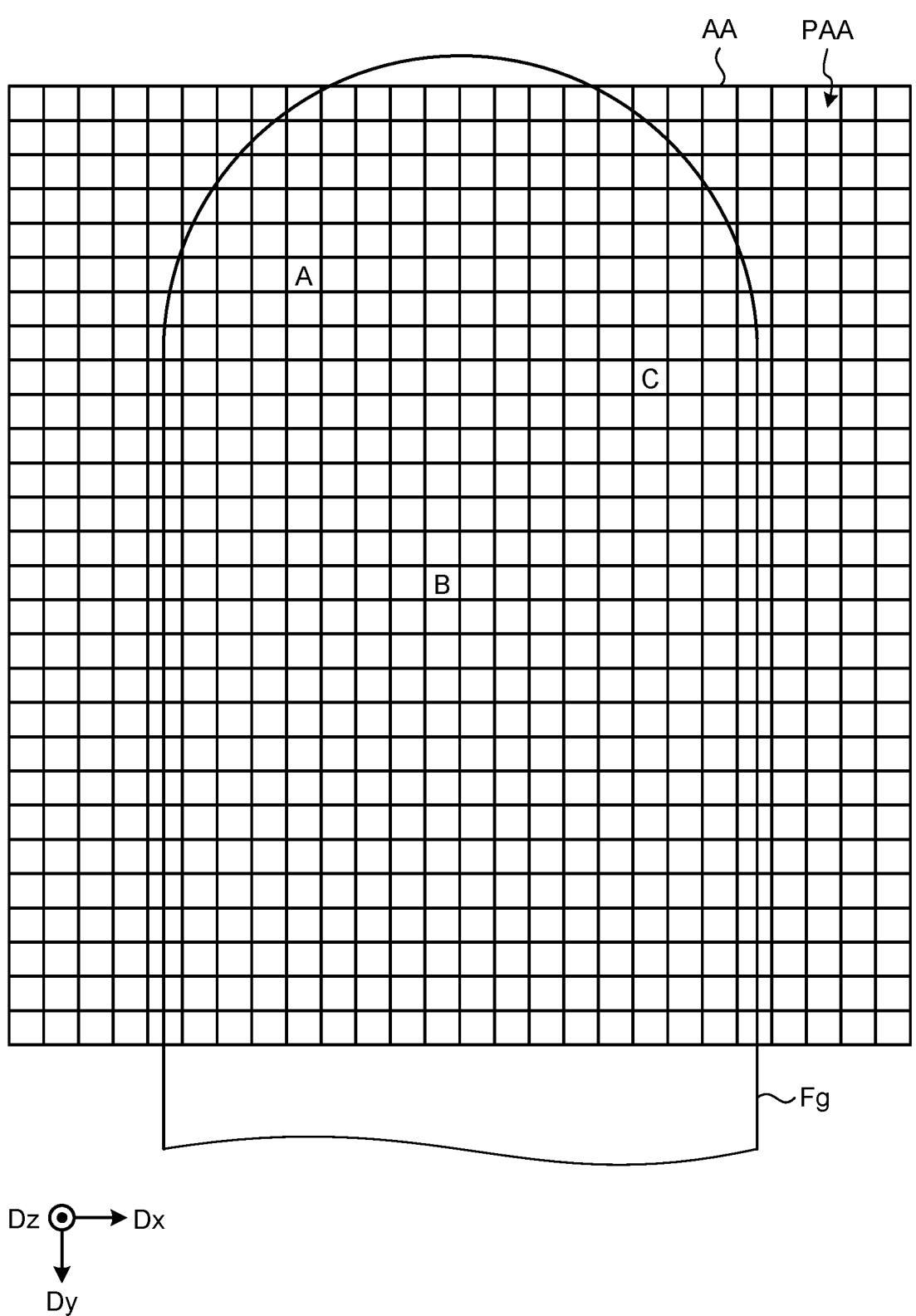
FIG. 15 is a schematic diagram illustrating a positional relation between a detection area of the sensor and an object to be detected.

FIG. 15 is a schematic diagram illustrating a positional relation between the detection area of the sensor and the object to be detected. FIG. 15 illustrates the finger Fg of the subject as the object to be detected.

Figure 16A:
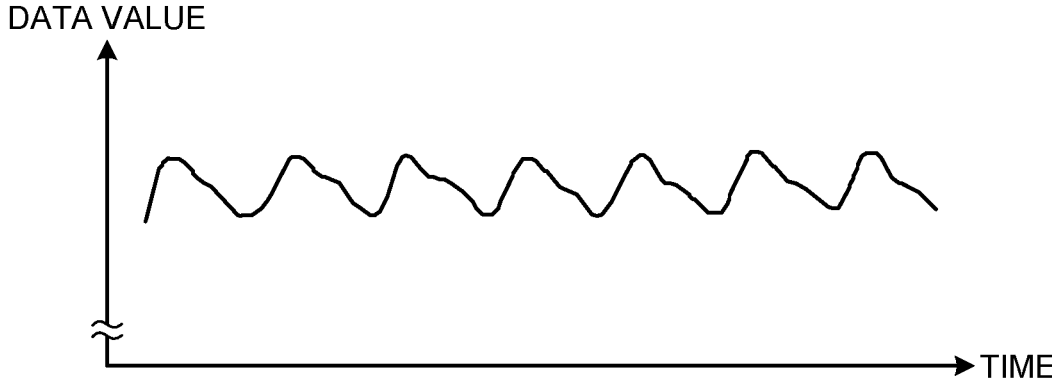
FIG. 16A is a diagram illustrating a waveform of a pulse wave acquired based on a detection signal detected in a partial detection area A illustrated in FIG. 15.
Figure 16B:
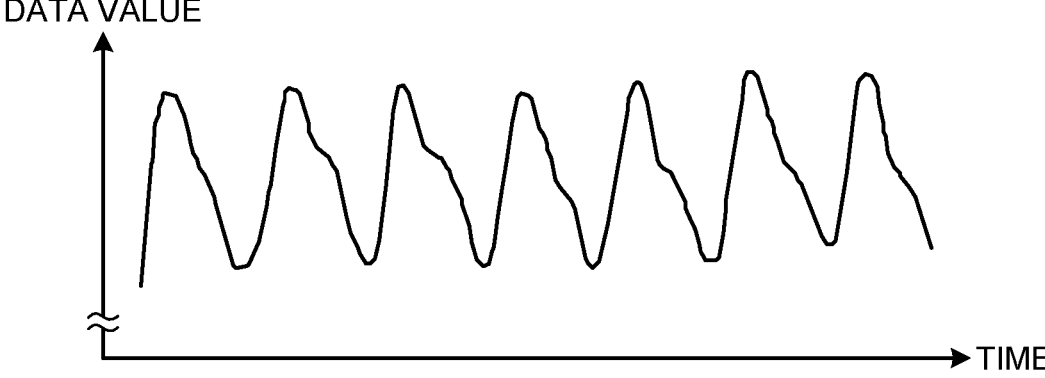
FIG. 16B is a diagram illustrating the waveform of the pulse wave acquired based on the detection signal detected in a partial detection area B illustrated in FIG. 15.
Figure 16C:
FIG. 16C is a diagram illustrating the waveform of the pulse wave acquired based on the detection signal detected in a partial detection area C illustrated in FIG. 15.

FIG. 16A is a diagram illustrating a waveform of a pulse wave acquired based on the detection signal detected in a partial detection area A illustrated in FIG. 15. FIG. 16B is a diagram illustrating the waveform of the pulse wave acquired based on the detection signal detected in a partial detection area B illustrated in FIG. 15. FIG. 16C is a diagram illustrating the waveform of the pulse wave acquired based on the detection signal detected in a partial detection area C illustrated in FIG. 15. In FIGS. 16A, 16B, and 16C, the horizontal axis represents time, and the vertical axis represents the data value of the pulse wave data.

Figure 17:
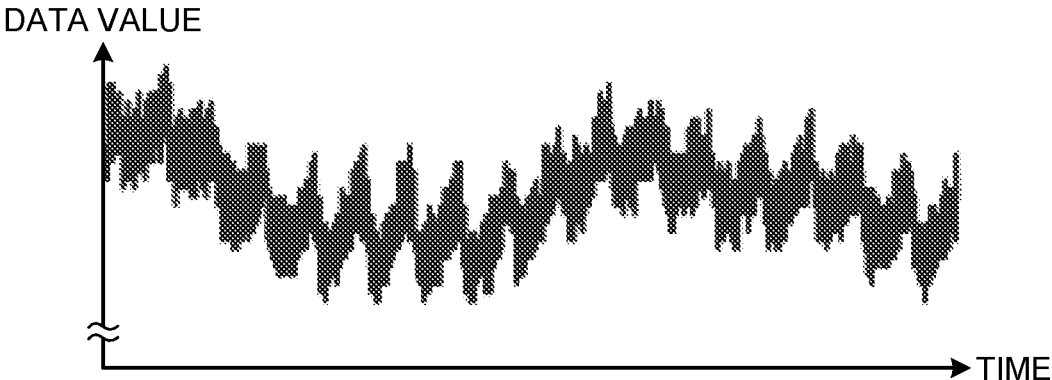
FIG. 17 is a diagram illustrating an exemplary detection signal waveform.

FIG. 17 is a diagram illustrating an exemplary detection signal waveform. In FIG. 17, the horizontal axis represents time, and the vertical axis represents the data value after A/D conversion of the detection signal Vdet.

In the following description, the magnitude of a peak-to-peak value (P-P value) of the data value in FIGS. 16A, 16B, 16C, and 17 is referred to as a "signal strength".

The strength of the signal detected in each of the partial detection areas PAA in the detection area AA differs depending on the distribution of subcutaneous blood vessels in the finger Fg of the subject. Specifically, for example, the signal strength of the pulse wave (FIG. 16B) acquired based on the detection signal Vdet detected in the partial detection area B illustrated in FIG. 15 is relatively larger than the signal strength of the pulse wave (FIG. 16A) acquired based on the detection signal Vdet detected in the partial detection area A illustrated in FIG. 15 and the signal strength of the pulse wave (FIG. 16C) acquired based on the detection signal Vdet detected in the partial detection area C illustrated in FIG. 15.

The detection signal Vdet detected in each of the partial detection areas PAA in the detection area AA includes noise components caused by disturbances and body movements of the subject, as illustrated in FIG. 17.

In the present disclosure, as preprocessing for acquiring the pulse wave data, extraction of one or more partial detection areas PAA is performed. The signal strength of the data acquired in each of the extracted partial detection areas PAA satisfies a predetermined condition. More specifically, from among the partial detection areas PAA in the detection area AA, one or more partial detection areas PAA are extracted in each of which data having relatively larger signal strength is acquired. Then, data on the living body (in this case, the pulse wave data) is acquired based on the detection signals Vdet detected in a biometric data acquisition area BAA including the one or more extracted partial detection areas PAA (refer to FIGS. 23A, 23B, and 23C). As a result, the accurate data on the living body can be acquired.

First Embodiment

Figure 18:
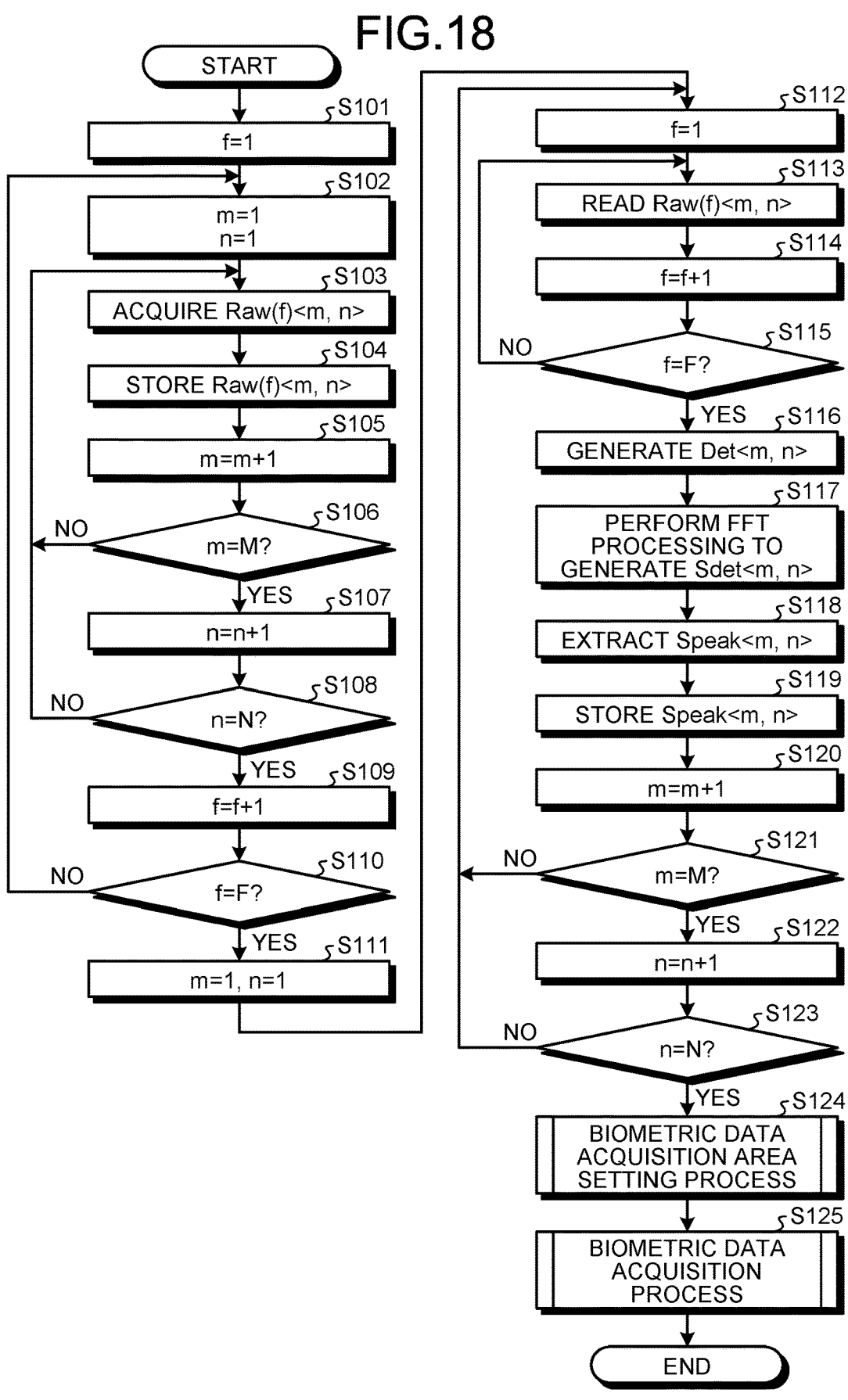
FIG. 18 is a flowchart illustrating an exemplary detection process in the detection device according to a first embodiment.

FIG. 18 is a flowchart illustrating an exemplary detection process in the detection device according to a first embodiment. Each process illustrated in FIG. 18 is mainly performed by the signal processor 44 of the detector 40.

In the following description, X<m, n> denotes a variable in the partial detection area PAA in the m-th column and the n-th row. The variable X<m, n> includes coordinate information on the partial detection area PAA from which the variable X<m, n> has been acquired. X(f)<m, n> denotes the variable X<m, n> in the f-th frame.

In the detection process illustrated in FIG. 18, the signal processor 44 first acquires detection values Raw(f)<m, n> for a plurality of frames in each of the partial detection areas PAA in the detection area AA. The number of frames F for which the detection values Raw(f)<m, n> are to be acquired is set to the number of times (for example, approximately 10 times) by which the peak of the pulse wave can be acquired. The number of frames F is stored in the storage 46, for example.

In processes from Step S102 to Step S110 of the detection process illustrated in FIG. 18, the control circuit 122 continuously turns on either the first light sources 61 or the second light sources 62, for example, during the periods t(1), t(2), t(3), and t(4) illustrated in FIG. 10. Each of the detection values Raw(f)<m, n> is temporarily stored in the storage 46, for example. FIG. 19 is a chart illustrating the detection values for the F frames in each of the partial detection areas in the detection area that are temporarily stored in the storage.

The signal processor 44 sets an initial frame f to 1 (f=1) (Step S101). The signal processor 44 sets m=1 and n=1 (Step S102), acquires the detection value Raw(f)<m, n> (Step S103), and temporarily stores the acquired detection value Raw(f)<m, n> in the storage 46 (Step S104).

The signal processor 44 then sets m=m+1 (Step S105) and determines whether m is M (m=M) (Step S106). If m is smaller than M (m<M) (No at Step S106), the step returns to the process at Step S103.

If m reaches M (m=M) (Yes at Step S106), the signal processor 44 then sets n=n+1 (Step S107) and determines whether n is N (n=N) (Step S108). If n is smaller than N (n<N) (No at Step S108), the step returns to the process at Step S103.

If n reaches N (n=N) (Yes at Step S108), the signal processor 44 then sets f=f+1 (Step S109) and determines whether f is F (f=F) (Step S110). If f is smaller than F (f<F) (No at Step S110), the step returns to the process at Step S102.

By repeating the above-described processes from Step S102 to Step S110 F times, the detection values Raw(f)<m, n> for the F frames in each of the partial detection areas PAA in the detection area AA illustrated in FIG. 19 are temporarily stored in the storage 46.

If f reaches F (f=F) (Yes at Step S110), the signal processor 44 then sets m=1 and n=1 (Step S111), sets the initial frame f to 1 (f=1) (Step S112), and reads the detection value Raw(f)<m, n> from the storage 46 (Step S113). Further, the signal processor 44 sets f=f+1 (Step S114) and determines whether f is F (f=F) (Step S115). If f is smaller than F (f<F) (No at Step S115), the step returns to the process at Step S113.

By performing the processes from Step S113 to Step S115 described above, the detection values Raw(f)<m, n> for the F frames in the partial detection area PAA in the m-th column and the n-th row are read.

Figure 20A:
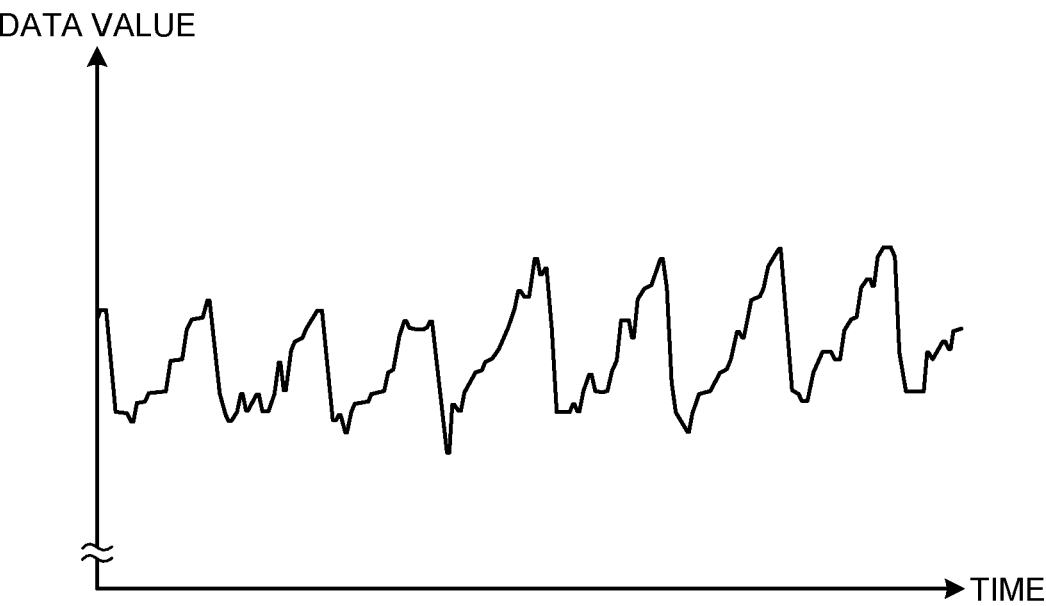
FIG. 20A is a diagram illustrating a specific example of time-domain data in each of the partial detection areas.
Figure 20B:
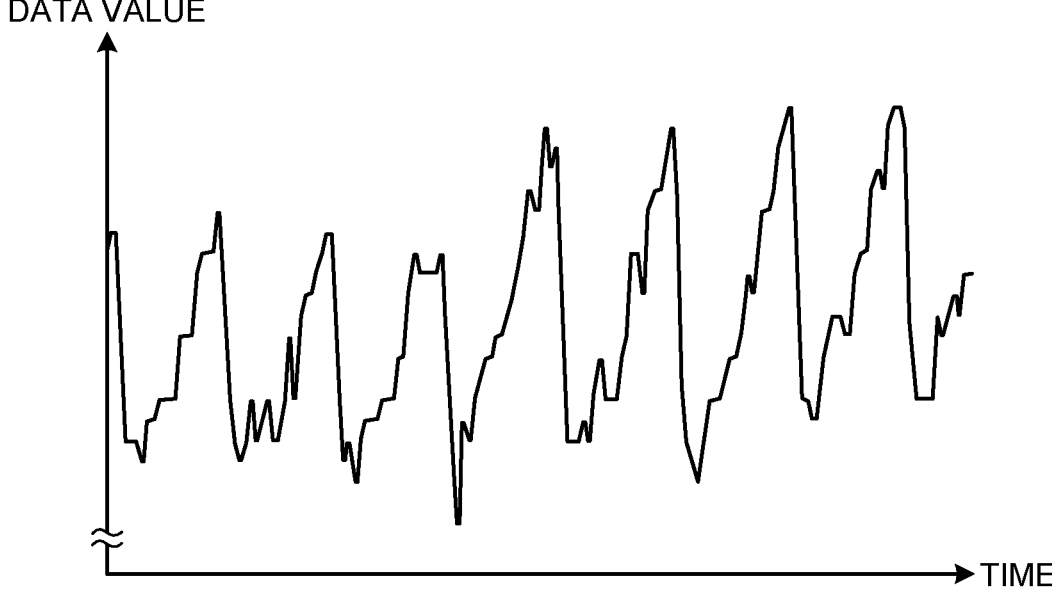
FIG. 20B is a diagram illustrating another specific example of the time-domain data in each of the partial detection areas.

If f reaches F (f=F) (Yes at Step S115), the signal processor 44 generates time-domain data Det<m, n> in the partial detection area PAA in the m-th column and the n-th row, based on the detection values Raw(f)<m, n> for the F frames read from the storage 46 (Step S116). FIGS. 20A and 20B are diagrams illustrating specific examples of the time-domain data in each of the partial detection areas. FIG. 20A illustrates an example of the time-domain data in the partial detection area A illustrated in FIG. 15. FIG. 20B illustrates an example of the time-domain data in the partial detection area B illustrated in FIG. 15.

Figure 21A:
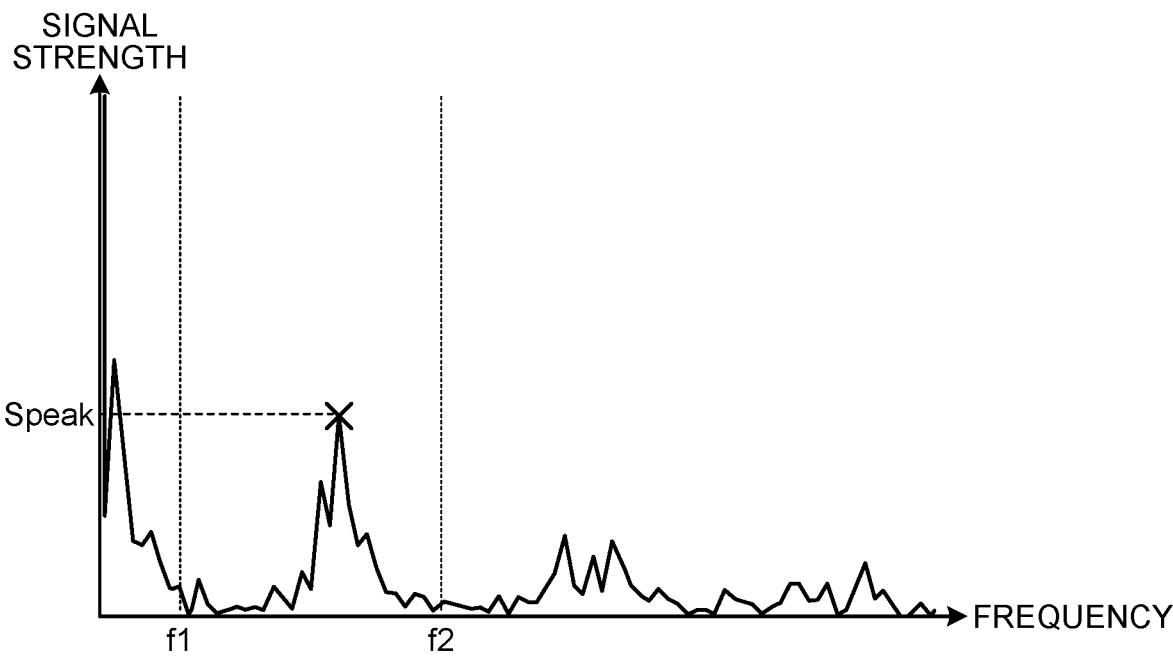
FIG. 21A is a diagram illustrating a specific example of frequency-domain data in each of the partial detection areas.
Figure 21B:
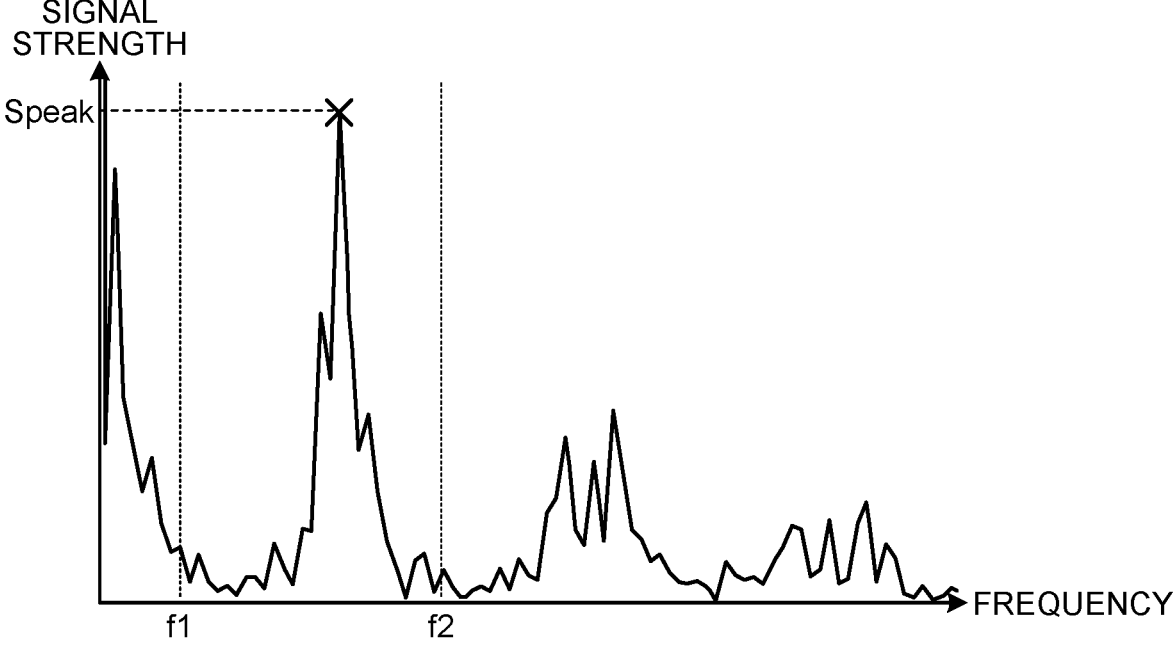
FIG. 21B is a diagram illustrating another specific example of the frequency-domain data in each of the partial detection areas.

The signal processor 44 performs Fourier transform processing (in this case, fast Fourier transform (FFT) processing) on the generated time-domain data Det<m, n> in the partial detection area PAA in the m-th column and the n-th row to generate frequency-domain data Sdet<m, n> (Step S117). FIGS. 21A and 21B are diagrams illustrating specific examples of the frequency-domain data in each of the partial detection areas. FIG. 21A illustrates an example of the frequency-domain data in the partial detection area A illustrated in FIG. 15. FIG. 21B illustrates an example of the frequency-domain data in the partial detection area B illustrated in FIG. 15.

The signal processor 44 extracts a peak value Speak<m, n> of the frequency-domain data in a frequency domain from a first frequency f1 to a second frequency f2 illustrated in FIGS. 21A and 21B (Step S118). The first frequency f1 is set to 0.5 Hz (f1=0.5 Hz), for example, and the second frequency f2 is set to 3 Hz (f2=3 Hz), for example. The signal processor 44 temporarily stores the extracted peak value Speak<m, n> in the storage 46 as the signal strength in the partial detection area PAA in the m-th column and the n-th row (Step S119).

The signal processor 44 then sets m=m+1 (Step S120) and determines whether m is M (m=M) (Step S121). If m is smaller than M (m<M) (No at Step S121), the step returns to the process at Step S112.

If m reaches M (m=M) (Yes at Step S121), the signal processor 44 then sets n=n+1 (Step S122) and determines whether n is N (n=N) (Step S123). If n is smaller than N (n<N) (No at Step S123), the step returns to the process at Step S112.

By repeating the above-described processes from Step S112 to Step S123 M×N times, the signal strength Speak<m, n> in each of the partial detection areas PAA in the detection area AA is temporarily stored in the storage 46.

Based on the signal strength Speak<m, n> in each of the partial detection areas PAA in the detection area AA extracted by the processing described above, the signal processor 44 sets the biometric data acquisition area for acquiring the pulse wave data (Step S124).

Figure 22:
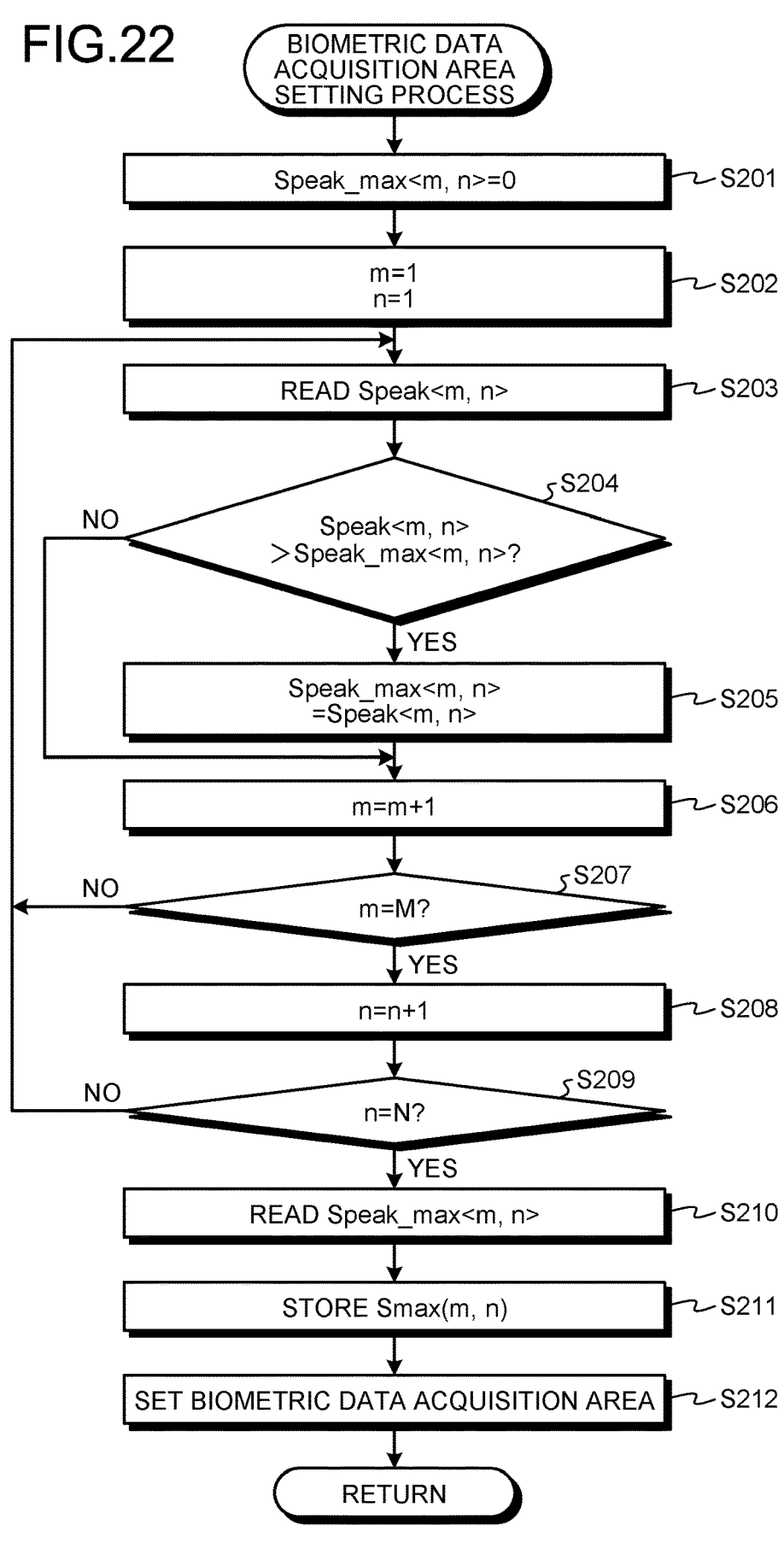
FIG. 22 is a flowchart illustrating an exemplary biometric data acquisition area setting process in the detection device according to the first embodiment.

FIG. 22 is a flowchart illustrating an exemplary biometric data acquisition area setting process in the detection device according to the first embodiment.

In the biometric data acquisition area setting process illustrated in FIG. 22, the signal processor 44 first performs comparison operations on the signal strengths Speak<m, n> in the respective partial detection areas PAA in the detection area AA and extracts coordinates of a position of the partial detection area PAA where the signal strength Speak<m, n> is maximal.

The signal processor 44 initializes a maximal signal strength Speak max<m, n> to be 0 (Speak max<m, n>=0) (Step S201). The signal processor 44 sets m=1 and n=1 (Step S202) and reads the signal strength Speak<m, n> (Step S203).

The signal processor 44 determines whether the read signal strength Speak<m, n> is higher than the maximal signal strength Speak max<m, n> (Speak<m, n>>Speak max<m, n>) (Step S204). If the signal strength Speak<m, n> is equal to or lower than the maximal signal strength Speak max<m, n> (Speak<m, n>≤Speak max<m, n>) (No at Step S204), the step proceeds to a process at Step S206.

If the read signal strength Speak<m, n> is higher than the maximal signal strength Speak max<m, n> (Speak<m, n>>Speak max<m, n>) (Yes at Step S204), the signal processor 44 replaces the maximal signal strength Speak max<m, n> with the signal strength Speak<m, n> (Speak max<m, n>=Speak<m, n>) and temporarily stores the replaced value in the storage 46 (Step S205).

The signal processor 44 then sets m=m+1 (Step S206) and determines whether m is M (m=M) (Step S207). If m is smaller than M (m<M) (No at Step S207), the step returns to the process at Step S203.

If m reaches M (m=M) (Yes at Step S207), the signal processor 44 then sets n=n+1 (Step S208) and determines whether n is N (n=N) (Step S209). If n is smaller than N (n<N) (No at Step S209), the step returns to the process at Step S203.

By repeating the above-described processes from Step S203 to Step S209 M×N times, the maximal signal strength Speak max<m, n> in the detection area AA and the coordinate information on the partial detection area PAA from which the maximal signal strength Speak max<m, n> has been acquired are temporarily stored in the storage 46.

If n reaches N (n=N) (Yes at Step S209), the signal processor 44 reads the maximal signal strength Speak max<m, n> temporarily stored in the storage 46 (Step S210) and stores signal strength maximum coordinates Smax(m, n) in the storage 46 (Step S211). The signal strength maximum coordinates Smax(m, n) is coordinates of the partial detection area PAA from which the maximal signal strength Speak max<m, n> has been acquired.

Figure 23A:
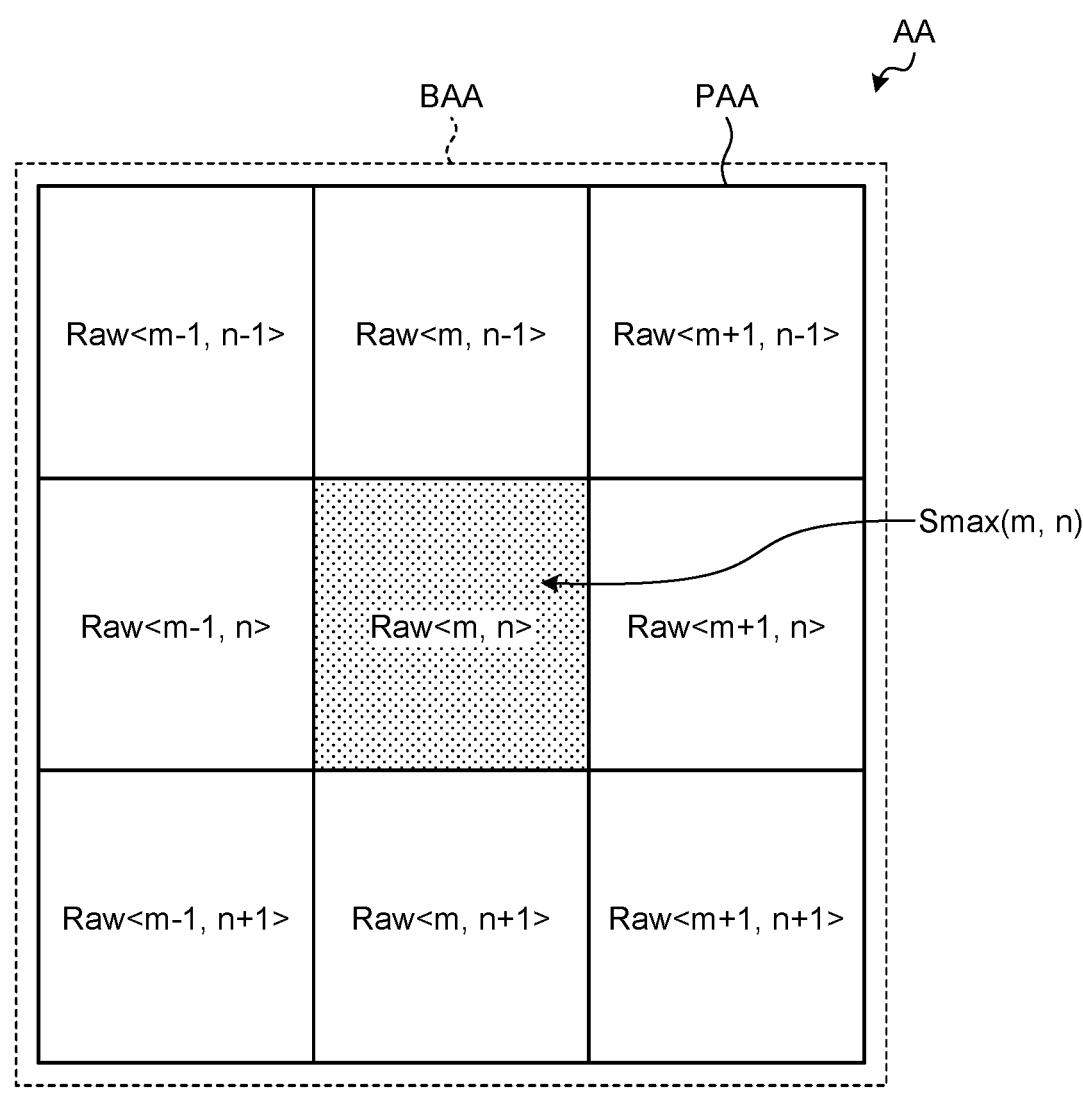
FIG. 23A is a diagram illustrating a specific example of a biometric data acquisition area.
Figure 23A:
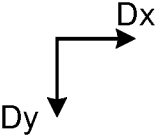
Figure 23B:
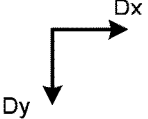
FIG. 23B is a diagram illustrating another specific example of the biometric data acquisition area.

The signal processor 44 sets a predetermined area including the signal strength maximum coordinates Smax(m, n) serving as the center coordinates thereof, as the biometric data acquisition area BAA (Step S212). FIGS. 23A, 23B, and 23C are diagrams illustrating specific examples of the biometric data acquisition area.

In an example illustrated in FIG. 23A, the biometric data acquisition area BAA includes three columns and three rows of the partial detection areas PAA centered on the partial detection area PAA located at the signal strength maximum coordinates Smax(m, n) in the detection area AA. In an example illustrated in FIG. 23B, the biometric data acquisition area BAA includes five columns and five rows of the partial detection areas PAA centered on the partial detection area PAA located at the signal strength maximum coordinates Smax(m, n) in the detection area AA. In an example illustrated in FIG. 23C, the biometric data acquisition area BAA includes seven columns and seven rows of the partial detection areas PAA centered on the partial detection area PAA located at the signal strength maximum coordinates Smax(m, n) in the detection area AA.

The biometric data acquisition area BAA is not limited to the aspects illustrated in FIGS. 23A, 23B, and 23C. The biometric data acquisition area BAA only needs to include at least the partial detection area PAA located at the signal strength maximum coordinates Smax(m, n) and may include, for example, only the partial detection area PAA located at the signal strength maximum coordinates Smax (m, n).

The biometric data acquisition area BAA set at Step S212 is stored in the storage 46.

Figure 24:
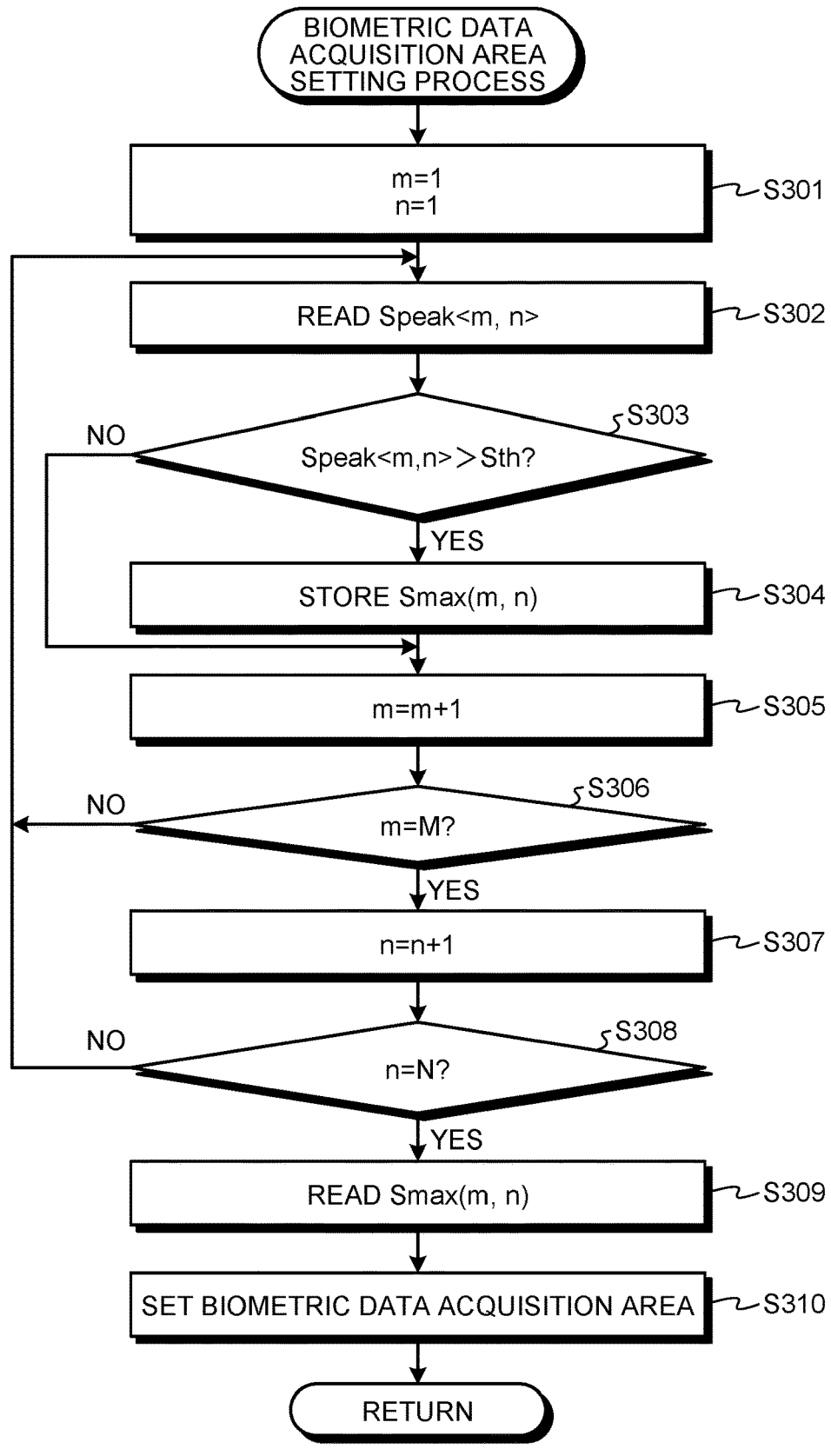
FIG. 24 is a flowchart illustrating an exemplary biometric data acquisition area setting process in the detection device according to a modification of the first embodiment.

The biometric data acquisition area setting process is not limited to the aspect illustrated in FIG. 22. FIG. 24 is a flowchart illustrating an exemplary biometric data acquisition area setting process in the detection device according to a modification of the first embodiment.

In the biometric data acquisition area setting process illustrated in FIG. 24, a predetermined signal strength threshold Sth for the signal strength is set in advance and stored in the storage 46. The signal processor 44 sets m=1 and n=1 (Step S301), reads the signal strength Speak<m, n> (Step S302), and determines whether the signal strength Speak<m, n> is higher than the signal strength threshold Sth (Speak<m, n>>Sth) (Step S303).

If the signal strength Speak<m, n> is equal to or lower than the signal strength threshold Sth (Speak<m, n>≤Sth) (No at Step S303), the step proceeds to a process at Step S305.

If the signal strength Speak<m, n> is higher than the signal strength threshold Sth (Speak<m, n>>Sth) (Yes at Step S303), the signal processor 44 stores, in the storage 46, the coordinates of the partial detection area PAA from which the signal strength Speak<m, n> has been acquired, such that the coordinates is handled as the signal strength maximum coordinates Smax(m, n) (Step S304).

The signal processor 44 then sets m=m+1 (Step S305) and determines whether m is M (m=M) (Step S306). If m is smaller than M (m<M) (No at Step S306), the step returns to the process at Step S302.

If m reaches M (m=M) (Yes at Step S306), the signal processor 44 then sets n=n+1 (Step S307) and determines whether n is N (n=N) (Step S308). If n is smaller than N (n<N) (No at Step S308), the step returns to the process at Step S302.

By repeating the above-described processes from Step S302 to Step S308 M×N times, the signal strength maximum coordinates Smax(m, n) in the detection area AA are stored in the storage 46.

The signal processor 44 reads the signal strength maximum coordinates Smax(m, n) stored in the storage 46 (Step S309) and sets the biometric data acquisition area BAA including the partial detection area PAA with the signal strength maximum coordinates Smax(m, n) (Step S310) in the same manner as in the biometric data acquisition area setting process illustrated in FIG. 22.

The biometric data acquisition area BAA set at Step S310 is stored in the storage 46. If more than one set of the signal strength maximum coordinates Smax(m, n) are extracted in the above-described processes from Step S302 to Step S308, more than one biometric data acquisition area BAA is set in the detection area AA.

One or more of the signal strength maximum coordinates Smax(m, n) only needs to be extracted in the detection area AA. For example, a plurality of sets of the signal strength maximum coordinates Smax(m, n) included in the highest predetermined percentage of all the signal strengths Speak<m, n> detected in the respective partial detection areas PAA in the detection area AA may be extracted.

Referring back to FIG. 18, in a biometric data acquisition process (Step S125), the signal processor 44 reads the biometric data acquisition area BAA stored in the storage 46 and acquires the pulse wave data based on the detection signals Vdet detected in the partial detection areas PAA included in the biometric data acquisition area BAA.

When more than one of the partial detection areas PAA are included in the biometric data acquisition area BAA as illustrated in FIGS. 23A, 23B, and 23C, or when more than one of the biometric data acquisition areas BAA are set in the detection area AA, the signal processor 44 acquires the pulse wave data by averaging the detection signals Vdet output from the partial detection areas PAA in the biometric data acquisition area or areas BAA. As a result, improvement in quality of the pulse wave data can be expected.

As described above, the strength of the signal detected in each of the partial detection areas PAA in the detection area AA differs depending on the distribution of the subcutaneous blood vessels in the finger Fg of the subject. The detection device 1 of the present embodiment extracts the partial detection areas PAA in each of which the signal strength of the data that is relatively larger are acquired in the detection area AA, and acquires the pulse wave data based on the detection signals Vdet detected in the biometric data acquisition area BAA including the extracted partial detection areas PAA (refer to FIGS. 23A, 23B, and 23C). As a result, the accurate pulse wave data can be acquired.

Second Embodiment

Figure 25:
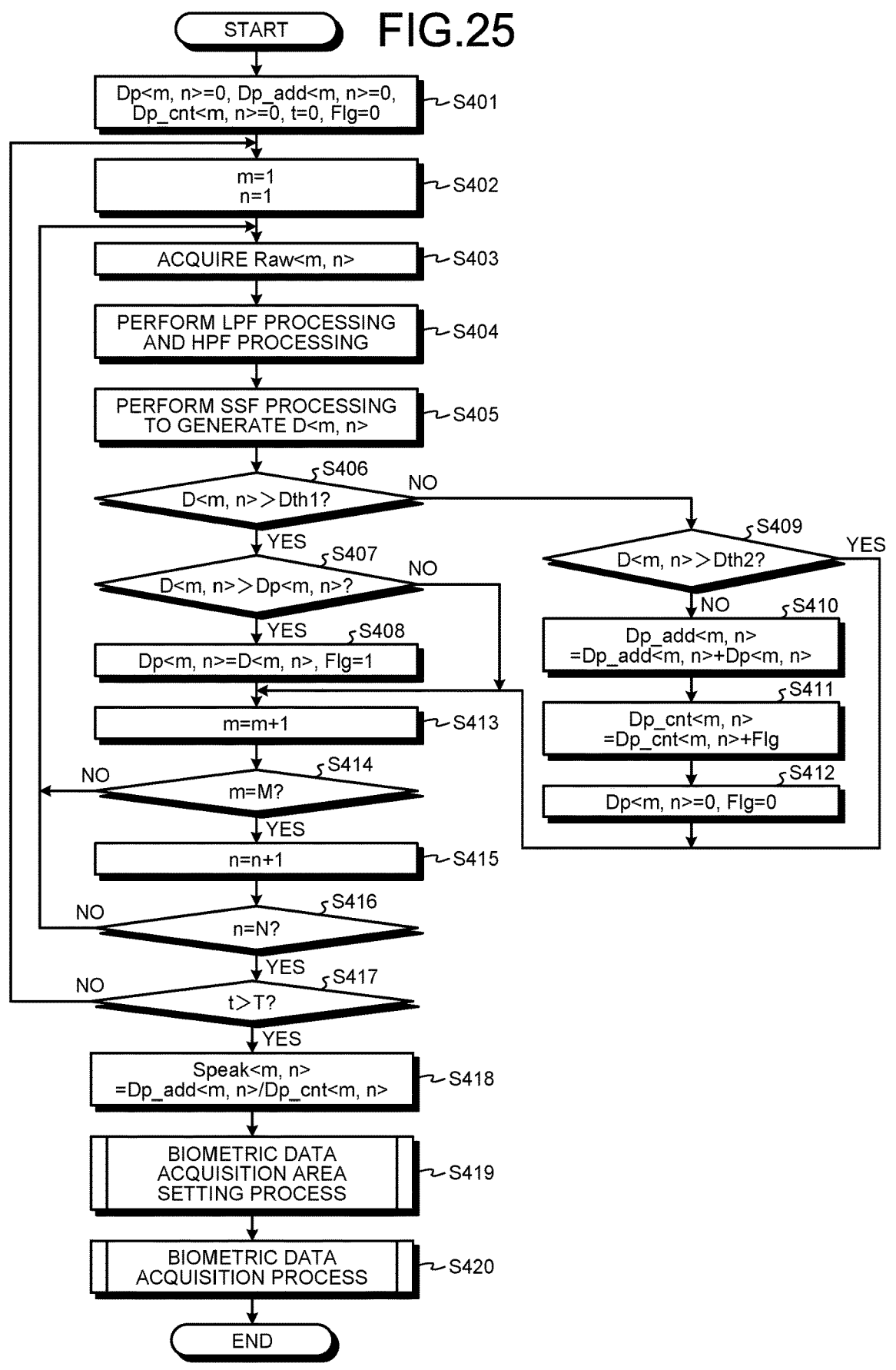
FIG. 25 is a flowchart illustrating an exemplary detection process in the detection device according to a second embodiment.

FIG. 25 is a flowchart illustrating an exemplary detection process in the detection device according to a second embodiment. The process illustrated in FIG. 25 is performed mainly by the signal processor 44.

Figure 26A:
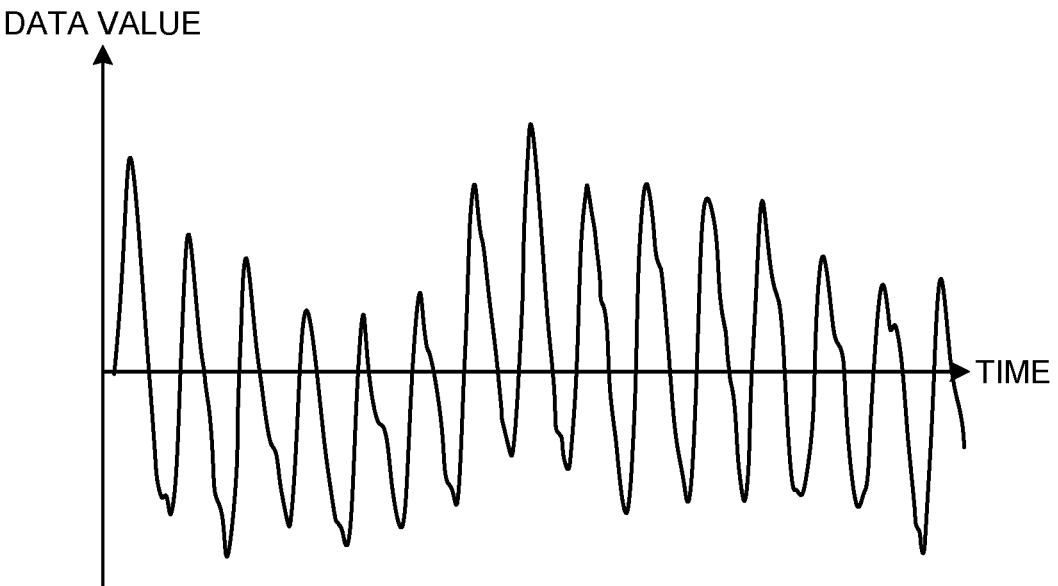
FIG. 26A is a diagram illustrating an example of data after being subjected to low-pass filter (LPF) processing and high-pass filter (HPF) processing.
Figure 26B:
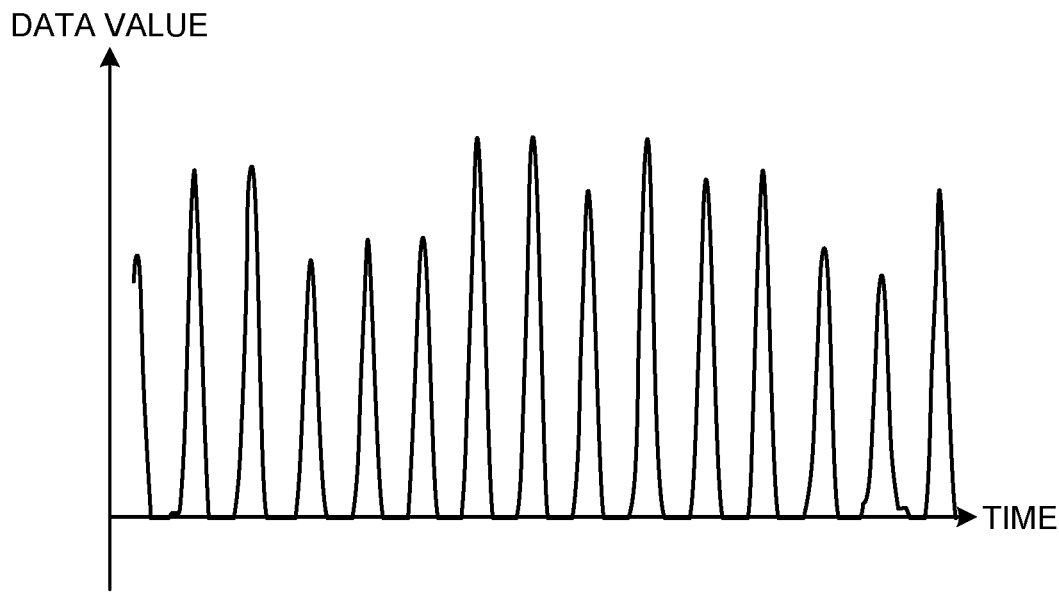
FIG. 26B is a diagram illustrating an example of data after being subjected to slope sum function (SSF) processing.

In the detection process illustrated in FIG. 25, the signal processor 44 acquires the detection value Raw<m, n> in each of the partial detection areas PAA in the detection area AA, performs low-pass filter (LPF) processing and high-pass filter (HPF) processing, and then performs predetermined peak detection processing. In this case, slope sum function (SSF) processing will be described as an example of data conversion processing used in the peak detection processing. FIG. 26A is a diagram illustrating an example of data after being subjected to the LPF processing and the HPF processing. FIG. 26B is a diagram illustrating an example of data after being subjected to the SSF processing.

In the SSF processing, the following arithmetic expressions are applied to the detection value Raw. In the following arithmetic expressions, $x_p$ denotes a data value obtained after the LPF processing and the HPF processing are performed on the detection value Raw, and $y_p$ denotes a data value D after being subjected to the SSF processing. P denotes the number of samples used for the SSF processing. The following arithmetic expressions are stored in the storage 46, for example. The number of samples P is stored in the storage 46, for example.

$$y_p \sum_{i=0}^{P-1} s_{p-i} \tag{1}$$

$$4 \le P \le 16$$

$$s_p = \begin{cases} x_p - x_{p-1} \, (x_p > x_{p-1}) \\ 0 \, (x_p \le x_{p-1}) \end{cases}$$

Figure 27:
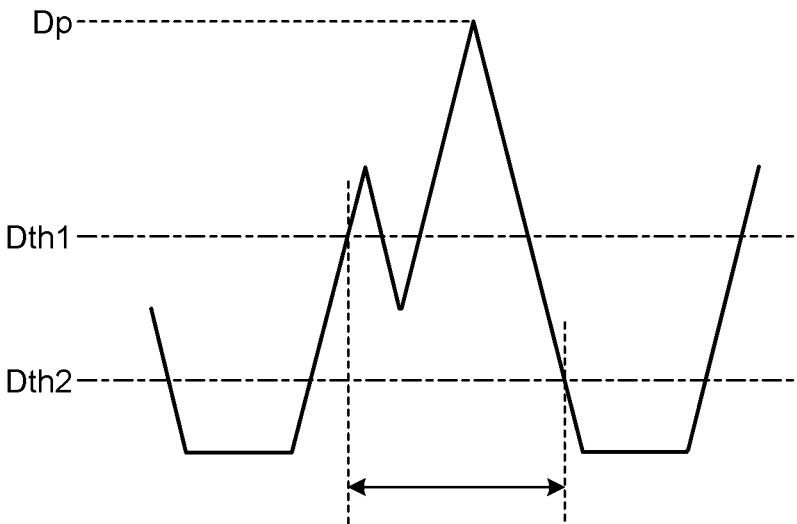
FIG. 27 is a conceptual diagram illustrating an exemplary peak detection method.

FIG. 27 is a conceptual diagram illustrating an exemplary peak detection method. In the signal processor 44, a first threshold Dth1 and a second threshold Dth2 (Dth1>Dth2) are set for the data value D after being subjected to the SSF processing. The first threshold Dth1 and the second threshold Dth2 are stored in the storage 46, for example.

During a period from when the data value D after being subjected to the SSF processing exceeds the first threshold Dth1 until it falls below the second threshold Dth2, the signal processor 44 detects a peak value Dp of the data value D after being subjected to the SSF processing and sequentially stores the peak value Dp temporarily in the storage 46.

The signal processor 44 accumulates the peak value Dp for each of the partial detection areas PAA in the detection area AA and temporarily stores the accumulated value in the storage 46. The signal processor 44 temporarily stores the number of times of accumulation (accumulation count) of the peak value Dp in the storage 46. FIG. 28A is a chart illustrating the accumulated peak values temporarily stored in the storage. FIG. 28B is a chart illustrating the peak accumulation counts temporarily stored in the storage.

The signal processor 44 divides an accumulated peak value Dp_add<m, n> (refer to FIG. 28A) by a peak accumulation count Dp_cnt<m, n> (FIG. 28B). The accumulated peak value Dp_add<m, n> is the accumulated value of the peak values Dp<m, n> detected during a predetermined peak detection period T. The peak accumulation count Dp_cnt<m, n> is the number of times of accumulation of the peak value Dp<m, n>. The signal processor 44 uses the division result as the signal strength Speak in each of the partial detection areas PAA to set the biometric data acquisition area in the same manner as that of the first embodiment. In the peak detection period T, a period during which the peak value Dp can be acquired a plurality of times (for example, approximately 10 times) is set and the values are stored in the storage 46.

First, as initial setting for the detection process illustrated in FIG. 25, the signal processor 44 resets the peak value Dp<m, n>, the accumulated peak value Dp_add<m, n>, the peak accumulation count Dp_cnt<m, n>, a timer value t for the peak detection period T, and a peak flag Flg (Dp<m, n>=0, Dp_add<m, n>=0, Dp_cnt<m, n>=0, t=0, Flg=0) for each of the partial detection areas PAA in the detection area AA (Step S401).

In the following processes from Step S402 to Step S417, the control circuit 122 continuously turns on either the first light sources 61 or the second light sources 62, for example, during the periods t(1), t(2), t(3), and t(4) illustrated in FIG. 10. Each of the detection values Raw<m, n> is temporarily stored in the storage 46, for example. Each of the detection values Raw<m, n> is stored for the number of samples P in the SSF processing, that is, for P frames.

The signal processor 44 sets m=1 and n=1 (Step S402), acquires the detection value Raw<m, n> (Step S403), and performs the LPF processing and the HPF processing on the acquired detection value Raw<m, n> (Step S404). This operation removes the direct-current (DC) component and noise components of the detection value Raw<m, n>.

The signal processor 44 performs the SSF processing using the arithmetic expressions given above on the data after being subjected to the LPF processing and the HPF processing to generate the data value D<m, n> (Step S405) and determines whether the data value D<m, n> is higher than the first threshold Dth1 (D<m, n>>Dth1) (Step S406).

If the data value D<m, n> is higher than the first threshold Dth1 (D<m, n>>Dth1) (Yes at Step S406), the signal processor 44 then determines whether the data value D<m, n> is higher than the peak value Dp<m, n> temporarily stored in the storage 46 (D<m, n>>Dp<m, n>) (Step S407).

If the data value D<m, n> is equal to or lower than the peak value Dp<m, n> (D<m, n>≤Dp<m, n>) (No at Step S407), the step proceeds to a process at Step S413.

If the data value D<m, n> is higher than the peak value Dp<m, n> (D<m, n>>Dp<m, n>) (Yes at Step S407), the signal processor 44 replaces the peak value Dp<m, n> with the data value D<m, n> (Dp<m, n>=D<m, n>), sets the peak flag Flg to "1" (Flg=1) and temporarily stores the replaced value in the storage 46 (Step S408).

If the data value D<m, n> is equal to or lower than the first threshold Dth1 (D<m, n>≤Dth1) (No at Step S406), the signal processor 44 then determines whether the data value D<m, n> is higher than the second threshold Dth2 (D<m, n>>Dth2) (Step S409).

If the data value D<m, n> is higher than the second threshold Dth2 (D<m, n>>Dth2) (Yes at Step S409), the step proceeds to the process at Step S413.

If the data value D<m, n> is equal to or lower than the second threshold Dth2 (D<m, n>≤Dth2) (No at Step S409), the signal processor 44 adds the peak value Dp<m, n> stored in a storage 46 to the accumulated peak value Dp_add<m, n> (Dp_add<m, n>=Dp_add<m, n>+Dp<m, n>) (Step S410) and adds the peak flag Flg (Flg=1) to the peak accumulation count Dp_cnt<m, n> (Dp_cnt<m, n>=Dp_cnt<m, n>+Flg) (Step S411). Then, the peak value Dp<m, n> and the peak flag Flg are reset (Dp<m, n>=0, and Flg=0) (Step S412), and the step proceeds to the process at Step S413.

The signal processor 44 then sets m=m+1 (Step S413) and determines whether m is M (m=M) (Step S414). If m is smaller than M (m<M) (No at Step S414), the step returns to the process at Step S403.

If m reaches M (m=M) (Yes at Step S414), the signal processor 44 then sets n=n+1 (Step S415) and determines whether n is N (n=N) (Step S416). If n is smaller than N (n<N) (No at Step S416), the step returns to the process at Step S403.

If n reaches N (n=N) (Yes at Step S416), the signal processor 44 then determines whether the timer value t exceeds the peak detection period T (t>T) (Step S417). If the timer value t is equal to or smaller than the peak detection period T (t≤T) (No at Step S417), the step returns to the process at Step S402.

By repeating the above-described processes from Step S402 to Step S417, the accumulated peak value Dp_add<m, n> (FIG. 28A) and the peak accumulation count Dp_cnt<m, n> (FIG. 28B) of the peak value Dp<m, n> in each of the partial detection areas PAA in the detection area AA detected in the peak detection period T are temporarily stored in the storage 46.

If the timer value t exceeds the peak detection period T (t>T) (Yes at Step S417), the signal processor 44 calculates the signal strength Speak<m, n> in each of the partial detection areas PAA in the detection area AA (Speak<m, n>=Dp_add<m, n>/Dp_cnt<m, n>) (Step S418).

The signal processor 44 sets the biometric data acquisition area for acquiring the pulse wave data based on the signal strength Speak<m, n> in each of the partial detection areas PAA in the detection area AA extracted by the process described above (Step S419). The signal processor 44 reads the biometric data acquisition area BAA stored in the storage 46 in the biometric data acquisition process (Step S420). The signal processor 44 acquires the pulse wave data based on the detection signals Vdet detected in the partial detection areas PAA included in the biometric data acquisition area BAA. As a result, the accurate pulse wave data can be acquired in the same manner as in the first embodiment. The biometric data acquisition area setting process (Step S419) and the biometric data acquisition process (Step S420) are the same as those in the first embodiment, and therefore, will not be described in detail.

In the embodiment described above, the example has been described in which the partial detection areas PAA are provided in a matrix having M columns and N rows configuration in the detection area AA. However, another configuration may be employed in which, for example, M partial detection areas PAA are arranged in the first direction Dx in the detection area AA. In this case, the biometric data acquisition area BAA only needs to include at least the partial detection area PAA located at the signal strength maximum coordinates Smax(m, 1). The biometric data acquisition area BAA may also include more than one and less than M, such as three, five, or seven, of the partial detection areas PAA centered on the partial detection area PAA located at the signal strength maximum coordinates Smax(m, 1). Still another configuration may be employed in which, for example, N of the partial detection areas PAA are arranged in the second direction Dy in the detection area AA. In this case, the biometric data acquisition area BAA only needs to include at least the partial detection area PAA located at the signal strength maximum coordinates Smax(1, n). The biometric data acquisition area BAA may also include more than one and less than N, such as three, five, or seven, of the partial detection areas PAA centered on the partial detection area PAA located at the signal strength maximum coordinates Smax(1, n).

While the preferred embodiments have been described above, the present invention is not limited to the embodiments described above. The content disclosed in the embodiments is merely an example, and can be variously modified within the scope not departing from the gist of the present invention. Any modifications appropriately made within the scope not departing from the gist of the present invention also naturally belong to the technical scope of the present invention. At least one of various omissions, substitutions, and changes of the components can be made without departing from the gist of the embodiments and the modifications described above.

What is claimed is:

1. A detection device comprising:
a sensor having a detection area divided into a plurality of partial detection areas; and
a detector configured to:
extract, from among the partial detection areas, one or more partial detection areas in each of which a signal strength of data satisfying a predetermined condition is acquired;
acquire biometric data on an object to be detected based on detection signals detected in a biometric data acquisition area including the extracted one or more partial detection areas;
perform peak detection processing on the data acquired in each of the partial detection areas within a predetermined period; and
regard a value obtained by dividing an accumulated value of peak values detected within the period by the number of times of detection of the peak, as the signal strength in each of the partial detection areas.

2. The detection device according to claim 1, wherein the detector is configured to extract one or more partial detection areas in which the signal strength of the data that is the largest is acquired, from among the partial detection areas.

3. The detection device according to claim 1, wherein the detector is configured to
generate frequency-domain data for each of the partial detection areas, and
regard a peak value of the frequency-domain data within a predetermined frequency range as the signal strength in each of the partial detection areas.

4. The detection device according to claim 3, wherein the detector is configured to regard a peak value of the frequency-domain data within a frequency range equal to or higher than 0.5 Hz and lower than 3 Hz as the signal strength in each of the partial detection areas.

5. The detection device according to claim 1, wherein the detector is configured to perform the peak detection processing on data after being subjected to slope sum function (SSF) processing in each of the partial detection areas.

6. The detection device according to claim 1, wherein the sensor comprises a plurality of optical sensors provided in the respective partial detection areas.

7. The detection device according to claim 6, wherein the optical sensors are organic photodiodes.

8. A detection device comprising
a sensor having a detection area divided into a plurality of partial detection areas; and
a detector configured to:
extract, from among the partial detection areas, one or more partial detection areas in each of which a signal strength of data satisfying a predetermined condition is acquired;
acquire biometric data on an object to be detected based on detection signals detected in a biometric data acquisition area including the extracted one or more partial detection areas, wherein
the partial detection areas are provided in a matrix having a row-column configuration in the detection area, and
the detector is configured to:
extract coordinates of a position of a partial detection area in which the signal strength is maximal by performing comparison operations on the signal strengths in the respective partial detection areas; and
set a predetermined area including the extracted coordinates serving as center coordinates of the predetermined area as the biometric data acquisition area.

9. The detection device according to claim 8, wherein the biometric data acquisition area includes at least the partial detection area located at the center coordinates.

10. The detection device according to claim 8, wherein the biometric data acquisition area includes more than one partial detection area including the partial detection area located at the center coordinates.

11. The detection device according to claim 10, wherein the biometric data acquisition area includes three columns and three rows of the partial detection areas centered on the partial detection area located at the center coordinates.

12. The detection device according to claim 10, wherein the biometric data acquisition area includes five columns and five rows of the partial detection areas centered on the partial detection area located at the center coordinates.

13. The detection device according to claim 10, wherein the biometric data acquisition area includes seven columns and seven rows of the partial detection areas centered on the partial detection area located at the center coordinates.

14. The detection device according to claim 10, wherein the detector is configured to acquire the biometric data by averaging the detection signals output from the partial detection areas in the biometric data acquisition area.

* * * * *